(12) United States Patent
Kobayashi et al.

(10) Patent No.: US 9,316,564 B2
(45) Date of Patent: *Apr. 19, 2016

(54) BLADE INSPECTION APPARATUS AND BLADE INSPECTION METHOD

(71) Applicant: OLYMPUS CORPORATION, Shibuya-ku, Tokyo (JP)

(72) Inventors: Eiichi Kobayashi, Tama (JP); Yutaka Konomura, Tachikawa (JP); Fumio Hori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,859

(22) Filed: Jul. 21, 2014

(65) Prior Publication Data

US 2015/0036150 A1 Feb. 5, 2015

(30) Foreign Application Priority Data

Jul. 30, 2013 (JP) .................................. 2013-157926

(51) Int. Cl.
*G01N 21/00* (2006.01)
*G01M 15/02* (2006.01)
(Continued)

(52) U.S. Cl.
CPC ............ *G01M 15/02* (2013.01); *A61B 1/0005* (2013.01); *A61B 1/00188* (2013.01); *G01B 11/14* (2013.01); *G01B 11/24* (2013.01); *G01N 21/954* (2013.01); *G02B 23/2423* (2013.01); *G02B 23/2476* (2013.01); *G02B 23/2484* (2013.01);

(Continued)

(58) Field of Classification Search
CPC ........... G82B 23/24; F81D 5/88; F81D 25/88; G81N 21/954; H04N 13/00; A61B 1/008; G06F 15/00; G01J 5/00
USPC ............ 356/241.1, 241.6, 614–615; 600/138, 600/114
See application file for complete search history.

(56) References Cited

U.S. PATENT DOCUMENTS 5,669,871 A * 9/1997 Sakiyama ..................... 600/117
5,693,003 A 12/1997 Woelfelschneider et al.
(Continued)

FOREIGN PATENT DOCUMENTS

DE 4439227 C1 1/1996
EP 2597273 A2 5/2013
(Continued)

OTHER PUBLICATIONS

Extended European Search Report (EESR) dated Dec. 4, 2014 issued in counterpart European Application No. 14178312.6.

*Primary Examiner* — Tarifur Chowdhury
*Assistant Examiner* — Isiaka Akanbi
(74) *Attorney, Agent, or Firm* — Holtz, Holtz & Volek PC

(57) ABSTRACT

A blade inspection apparatus has a borescope and a PC. The borescope has a distance sensor for detecting an insertion length when an insertion section of the borescope is inserted through a hole provided in a casing in which a rotor of an engine is housed, an acceleration sensor for detecting an attitude of the insertion section, and distance sensors for detecting two distances from the insertion section to two stator vanes on a stator. The PC compares the insertion length, attitude and two distances detected in the borescope with the insertion length, attitude and two distances relating to an inspection image stored in a HDD. When a match occurs therebetween, the PC outputs match information.

16 Claims, 15 Drawing Sheets

(51) Int. Cl.
  *G01B 11/24* (2006.01)
  *G02B 23/24* (2006.01)
  *G01N 21/954* (2006.01)
  *G01B 11/14* (2006.01)
  *A61B 1/00* (2006.01)
  *F01D 21/00* (2006.01)

(52) U.S. Cl.
  CPC ........... *A61B 1/00177* (2013.01); *F01D 21/003* (2013.01); *G01N 2021/9542* (2013.01)

(56) References Cited

U.S. PATENT DOCUMENTS

| | | |
|---|---|---|
| 7,518,632 B2 | 4/2009 | Konomura |
| 8,314,834 B2 | 11/2012 | Konomura |
| 2004/0183900 A1 | 9/2004 | Karpen et al. |
| 2006/0140754 A1* | 6/2006 | Tanioka ............... 415/173.1 |
| 2007/0171406 A1* | 7/2007 | Stokes ................ 356/241.1 |
| 2011/0026805 A1* | 2/2011 | Hori ..................... 382/141 |
| 2012/0209069 A1 | 8/2012 | Popovic et al. |
| 2013/0135457 A1 | 5/2013 | Kell et al. |
| 2014/0253715 A1* | 9/2014 | Hori et al. ................ 348/82 |
| 2015/0002841 A1* | 1/2015 | Konomura et al. ....... 356/241.6 |
| 2015/0035969 A1* | 2/2015 | Kobayashi et al. ........ 348/82 |

FOREIGN PATENT DOCUMENTS

| | | |
|---|---|---|
| GB | 2493770 | 2/2013 |
| JP | 2007163723 A | 6/2007 |
| WO | 2011055245 A1 | 5/2011 |

* cited by examiner

FIG.17

| IMAGE ID | SCOPE ID | INSERTION LENGTH | ANGLE OF ELEVATION | ANGLE OF ROTATION | FIRST DISTANCE | SECOND DISTANCE |
|---|---|---|---|---|---|---|
| 00001 | 00101 | ... | ... | ... | ... | ... |
| 00002 | 00102 | ... | ... | ... | ... | ... |
| ... | ... | ... | ... | ... | ... | ... |

81

BLADE INSPECTION APPARATUS AND BLADE INSPECTION METHOD

CROSS REFERENCE TO RELATED APPLICATION

This application claims benefit of Japanese Application No. 2013-157926 filed in Japan on Jul. 30, 2013, the entire contents of which are incorporated herein by this reference.

BACKGROUND OF THE INVENTION

1. Field of the Invention

The present invention relates to a blade inspection apparatus and a blade inspection method for inspecting blades of an engine.

2. Description of the Related Art

Inspections of blades of jet engines or the like have been conventionally performed. An inspector performs a blade inspection, for example, by inserting an insertion section of a borescope, i.e., an endoscope, into an engine from an access port provided in the casing of the engine and by producing on a monitor a display of an endoscopic image of a blade in the engine.

An endoscopic apparatus has been proposed with which automation of the inspection process (labor saving) is performed so that the number of inspection process steps in inspection of blades of an engine is reduced, as disclosed in Japanese Patent Application Laid-Open Publication No. 2007-163723, thereby enabling reduction of the complicatedness in an object inspection. Ordinarily, however, a blade inspection is performed with a borescope held by an inspector.

When a defective is found in a blade by inspection, a need may arise to produce an enlarged display of the defective portion and examine the defective portion in detail, depending on the size of the defect. Therefore, borescopes of various view angles are provided. An inspector first inspects a blade through a large area by using a borescope of a wide view angle and thereafter performs a detailed inspection by using a borescope of a narrow view angle and displaying an enlarged image of a defective portion on a monitor. An observation window through which light is received from the object is disposed in a distal end portion in the insertion section of the borescope.

SUMMARY OF THE INVENTION

A blade inspection apparatus according to one aspect of the present invention is a blade inspection apparatus for inspecting a plurality of blades periodically disposed on a periphery of a rotating shaft of a rotor of an engine and rotated on the rotating shaft, the apparatus including a first attitude detection section provided in a first endoscope having a first insertion section, the first attitude detection section detecting a first attitude of the first insertion section, and a first distance detection section provided in the first endoscope, the first distance detection section detecting two first distances from the first insertion section to two objects along two directions perpendicular to an axis of the first insertion section and opposite to each other.

A blade inspection method according to another aspect of the present invention is a blade inspection method of inspecting a plurality of blades periodically disposed on a periphery of a rotating shaft of a rotor of an engine and rotated on the rotating shaft, the method including detecting a first attitude of a first insertion section of a first endoscope with a first attitude detection section provided in the first endoscope, and detecting two first distances from the first insertion section to two objects along two directions perpendicular to an axis of the first insertion section and opposite to each other with a first distance detection section provided in the first endoscope.

BRIEF DESCRIPTION OF THE DRAWINGS

FIG. 17 is a diagram showing the data structure of a photographing information recording file according to the first embodiment;

DETAILED DESCRIPTION OF THE PREFERRED EMBODIMENTS

Embodiments of the present invention will be described below with reference to the drawings.

First Embodiment

Entire Construction

Figure 1:
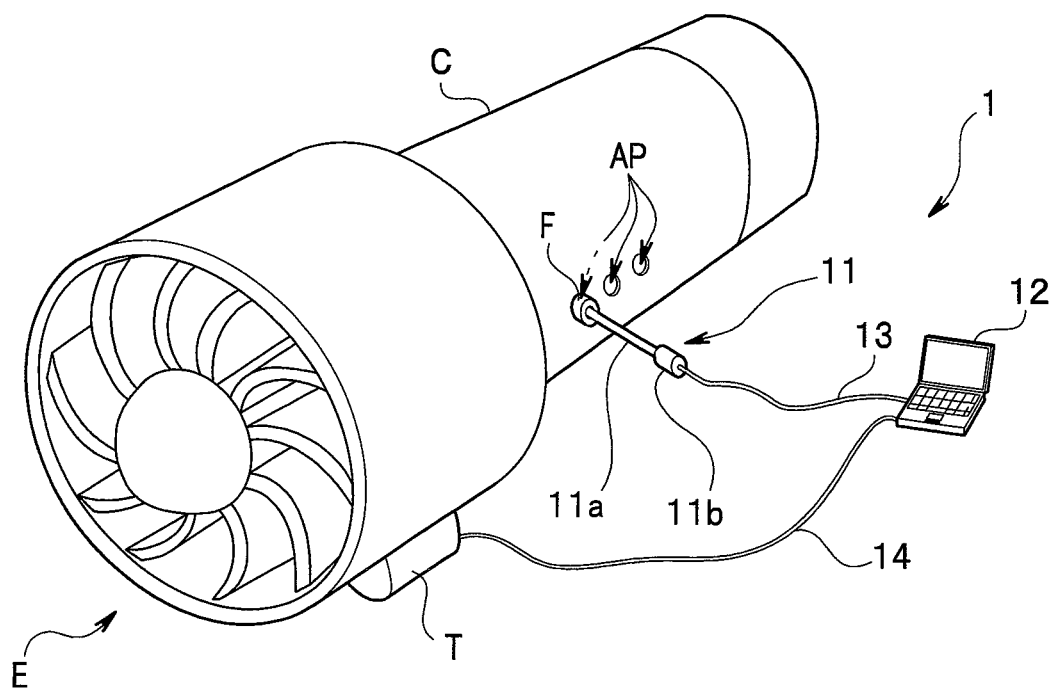
FIG. 1 is a perspective view for explaining a state of inspection of an engine according to a first embodiment of the present invention.
Figure 12:
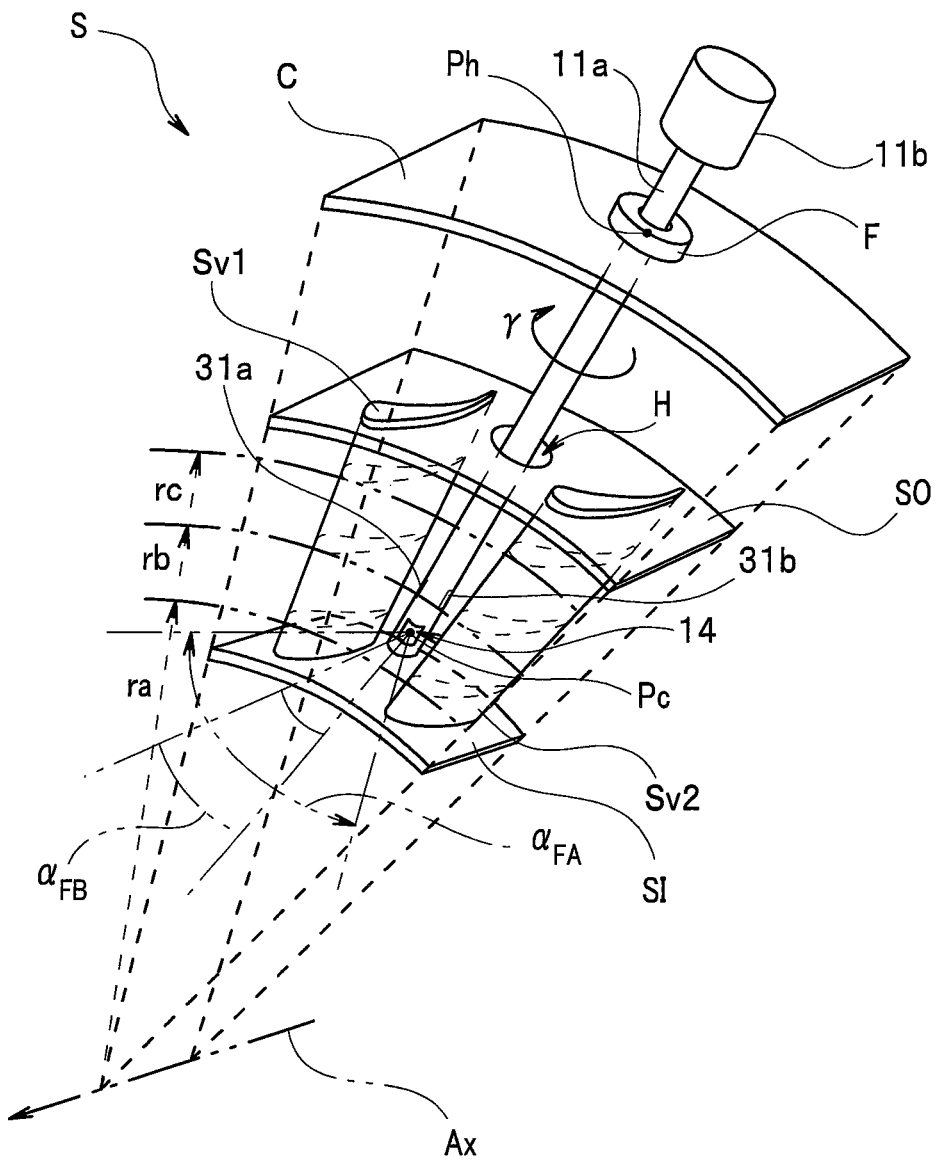
FIG. 12 is a perspective view of a portion of a stator S for explaining a state where an insertion section 11a is inserted in a casing C of an engine E according to the first embodiment.

FIG. 1 is a perspective view for explaining a state of inspection of an engine according to the present embodiment. In the present embodiment, an engine E is a jet engine. Description will be made of a case where a plurality of compressor blades (hereinafter referred to simply as "blades") in a compressor portion provided at the rear of an air intake portion are inspected with a blade inspection system. A turning tool T is connected to the engine E to enable a rotor R (FIG. 13) on which the plurality of blades are fixed to be rotated on an axis of rotation Ax (FIG. 12).

Note that while an example of inspection of the compressor blades is described below, inspection of other blades such as turbine blades can also be performed with the blade inspection system 1 in the present embodiment in the same manner.

The blade inspection system 1 includes a borescope 11 and a personal computer (hereinafter referred to as "PC") 12. The borescope 11 and the PC 12 are connected to each other through a signal cable (hereinafter referred to as "cable") 13. The borescope 11 has an insertion section 11a to be inserted into the engine E having a plurality of blades B to be inspected, and a grasping section 11b provided on a proximal end portion of the insertion section 11a.

The turning tool T and the PC 12 are connected to each other by a cable 14. The turning tool T is controlled according to an instruction from the PC 12 so as to rotate the rotor.

A casing C of the engine E has a plurality of (three in this example) access ports AP at predetermined positions. The insertion section 11a of the borescope 11 is an elongated rigid endoscope having such a diameter and length as to be capable of being inserted into the casing C through holes of any of the access ports AP to enable observation of the plurality of blades B disposed periodically about the axis of rotation Ax of the rotor R of the engine E.

When the insertion section 11a of the borescope 11 is inserted into the casing C, a fixing implement F is attached to the access port AP through which the insertion section 11a is to be inserted. The fixing implement F is an article of equipment for supporting and fixing the insertion section 11a of the borescope 11 at the position of the access port AP of the casing C. That is, the fixing implement F is constructed so as to be capable of being attached to the access port AP, to have an insertion hole through which the insertion section 11a is passed and to be capable of supporting the borescope 11.

The fixing implement F does not firmly fix the insertion section 11a of the borescope 11. The fixing implement F supports the insertion section 11a in the insertion hole of the fixing implement F while maintaining the insertion section 11a in a state of being fitted in the insertion hole with such a degree of looseness that the position of the distal end portion of the insertion section 11a can be changed, as described below.

Accordingly, a user as an inspector who inspects blades can insert the insertion section 11a into the insertion hole of the fixing implement F, insert the insertion section 11a into the engine E while holding the borescope 11 with his/her hand, move the insertion section 11a to and fro along the insertion direction in the engine E, and freely rotate the borescope 11 about the axis of the insertion section 11a. Further, the user can change the position of the distal end portion of the insertion section 11a.

As described above, the blade inspection system 1 is a blade inspection apparatus for inspecting the plurality of blades B periodically disposed about the axis of rotation Ax of the rotor R of the engine E and rotating about the axis of rotation Ax.

(Construction of the Borescope)

Figure 2:
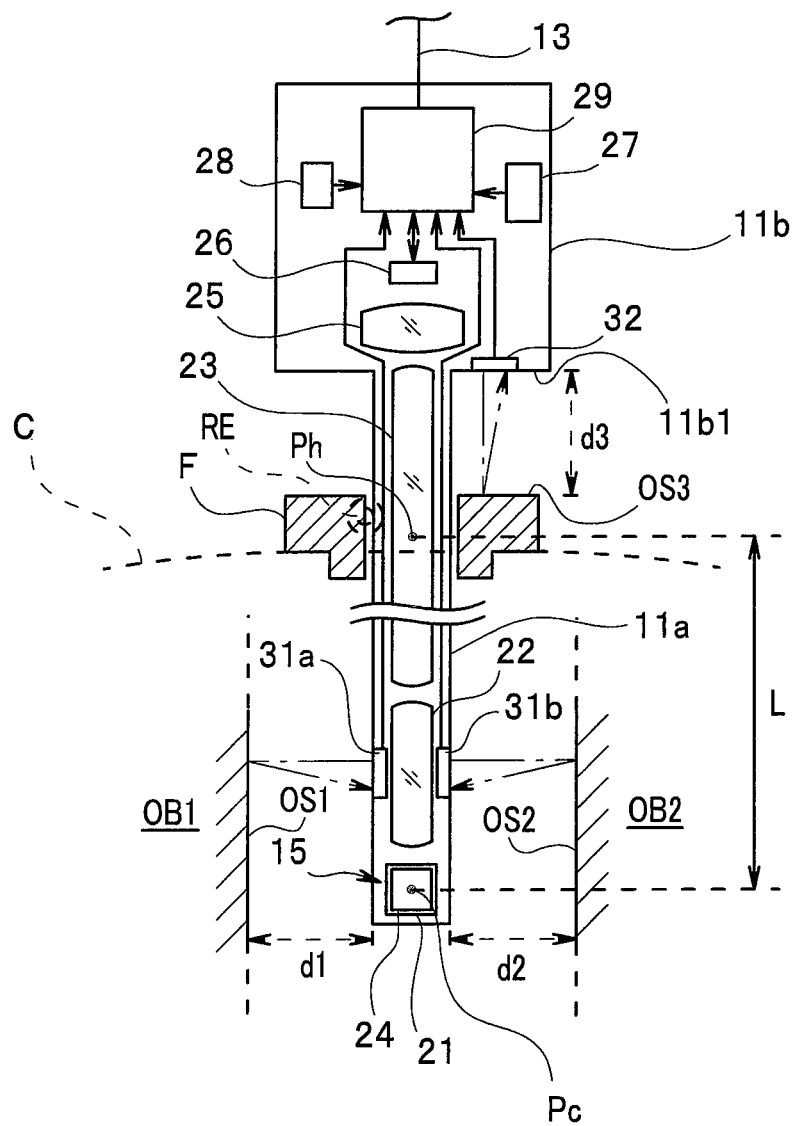
FIG. 2 is a diagram for explaining the construction of a borescope 11 according to the first embodiment.

FIG. 2 is a diagram for explaining the construction of the borescope 11.

An optical system for leading reflected light from an object to an image pickup device is disposed in the insertion section 11a. This optical system has a mirror 21, an objective optical system 22 and a relay optical system 23 disposed in the insertion section 11a. The mirror 21 is an optical component disposed in the distal end portion of the insertion section 11a. The mirror 21 directs toward the grasping section 11b light having entered through a glass plate 24 provided in an observation window 15 provided in a side surface of the distal end portion of the insertion section 11a. The objective optical system 22 is disposed in the insertion section 11a on the distal end side. The objective optical system 22 is an optical component for forming a real image of an object. The relay optical system 23 is an optical component for transmitting an image formed by the objective optical system 22 to the grasping section 11b.

Thus, the borescope 11 is a side-view type of endoscope provided with the observation window 15 in the distal end portion of the cylindrical insertion section 11a and the transparent glass member 24 in the observation window 15, and constructed so that light having been incident on the observation window 15 is incident on the mirror 21.

Note that an illumination device not illustrated is provided in the borescope 11. An object in such a position as to be opposed to the observation window 15 is illuminated with the illumination device. For example, the illumination device is constituted by a light source provided in the grasping section 11b and a light guide inserted in the insertion section 11a. The illumination device is provided so that light from the light source is emitted from the distal end portion of the insertion section 11a toward an object.

Two distance sensors 31a and 31b are disposed in the vicinity of the observation window 15 in the distal end portion of the insertion section 11a at a predetermined distance from the observation window 15. The direction along which reflected light from an object is incident on the mirror 21 is perpendicular to a line connecting centers of the two distance sensors 31a and 31b. A distance sensor 32 is disposed in the grasping section 11b.

In the grasping section 11b, an image pickup optical system 25, a CCD 26, which is an image pickup device, an acceleration sensor 27, an ID storage unit 28 and a communication control unit 29 are provided.

The image pickup optical system 25 is an optical system that forms on an image pickup surface of the CCD 26 an object image emitted from the relay optical system 23. The CCD 26, which is an area sensor, is a solid-state image pickup device that makes photoelectric conversion of an object image formed by the image pickup optical system 25.

Note that while the CCD 26 is provided in the grasping section 11b and disposed so as to receive light having passed through the optical system in the insertion section 11a in the present embodiment, the CCD 26 may alternatively be provided in the distal end portion of the insertion section 11a.

The acceleration sensor 27 is a three-axis acceleration sensor. The communication control unit 29 calculates an angle of elevation $\beta$ which is an inclination of the borescope 11 from the direction of gravity g and an angle of rotation $\gamma$ of the borescope 11 about the axis from outputs from the acceleration sensor 27, as described below.

The ID storage unit 28 is a storage unit that stores a scope ID as information for identification of the borescope 11.

The communication control unit 29 includes a central processing unit (CPU) and a communication interface unit. The configuration of the communication control unit 29 is described later.

The distance sensors 31a, 31b, and 32 are sensors that sense the distances to a surface of objects existing at such positions as to be opposed to the sensors. The distance sensors 31a, 31b, and 32 are, for example, each a PSD distance sensor having a light source element that projects a spot of light and a position sensitive detector (PSD) element that detects the position of the centroid of a received spot of light. The PSD distance sensor detects the distance to the object by using the principle of triangulation.

In the present embodiment, the distance sensors 31a and 31b are detection units that are disposed at positions on the surface of the insertion section 11a symmetric about the axis of the insertion section 11a, and that respectively detect the distances to objects existing opposite from each other along a direction perpendicular to the axis of the insertion section 11a.

Accordingly, when as shown in FIG. 2 the insertion section 11a is positioned between two objects B1 and OB2 so that the two distance sensors 31a and 31b can detect distances d1 and d2 to the two objects OB1 and OB2, the distance sensor 31a detects the distance d1 from the surface of the insertion section 11a to a surface OS1 of the first object OB1, and the distance sensor 31b detects the distance d2 from the surface of the insertion section 11a to a surface OS2 of the second object OB2. Each of the two distance sensors 31a and 31b measures the distance, for example, in a range of about 10 to 50 mm. That is, the distance sensors 31a and 31b are provided in the borescope 11, which is an endoscope, and constitute distance detection units that detect the two distances from the insertion section 11a to two objects (stator vanes Sv provided on a stator S of the engine E in this example) along two directions opposite to each other and perpendicular to the axis of the insertion section 11a.

In the present embodiment, the insertion section 11a is inserted between two stator vanes Sv of a stator S (FIG. 12) as described below. Accordingly, the surface OS1 of the first object OB1 is a surface of one stator vane Sv1 and the surface OS2 of the second object OB2 is a surface of the stator vane Sv2 adjacent to the first object OS1.

As described above, the two distance sensors 31a and 31b are provided on the side surface of the distal end portion of the insertion section 11a. The direction toward the object B1 detected with the distance sensor 31a is perpendicular to the axis of the insertion section 11a and is opposite to the direction toward the object OB2 detected with the distance sensor 31b. The distance sensor 31a detects the distance d1 to the surface OS1, and the distance sensor 31b detects the distance d2 to the surface OS2.

The distance sensor 32 is provided on a surface 11b1 of the grasping section 11b on the insertion section 11a side (i.e., on the distal end side). As shown in FIG. 2, the distance sensor 32 detects a distance d3 from the surface 11b1 on the insertion section 11a side, i.e., on the distal end side, to a surface OS3 of the fixing implement F. That is, when the insertion section 11a is inserted into the engine E, the distance sensor 32 outputs a detection signal according to the distance to the surface OS3 of the fixing implement F. The distance sensor 32 measures the distance, for example, in a range of about 300 mm at the maximum. The communication control unit 29 calculates an insertion length L of the insertion section 11a based on the detection output from the distance sensor 32, as described below.

That is, the distance sensor 32 and the communication control unit 29 are provided in the borescope 11, which is the endoscope having the insertion section 11a, and constitute an insertion length detection unit that detects the insertion length L of the insertion section 11a when the insertion section 11a is inserted from the access port AP, which is a hole provided in the casing C in which the rotor R is housed.

Note that while a PSD distance sensor is used as distance sensor 32 in the present embodiment, the system may alternatively be such that an encoder RE such as a roller encoder is provided on the fixing implement F, for example, as indicated by a broken line in FIG. 2; an output from the roller encoder RE is supplied to the PC 12 through a signal line led out from the roller encoder RE; and the insertion length L of the insertion section 11a is calculated from the output from the roller encoder RE in the PC 12.

Detection signals from the three distance sensors 31a, 31b, and 32 and an image signal from the CCD 26 and respective detection signals from the acceleration sensor 27 and a scope ID signal from the ID storage unit 28 are inputted to the communication control unit 29.

Figure 3:
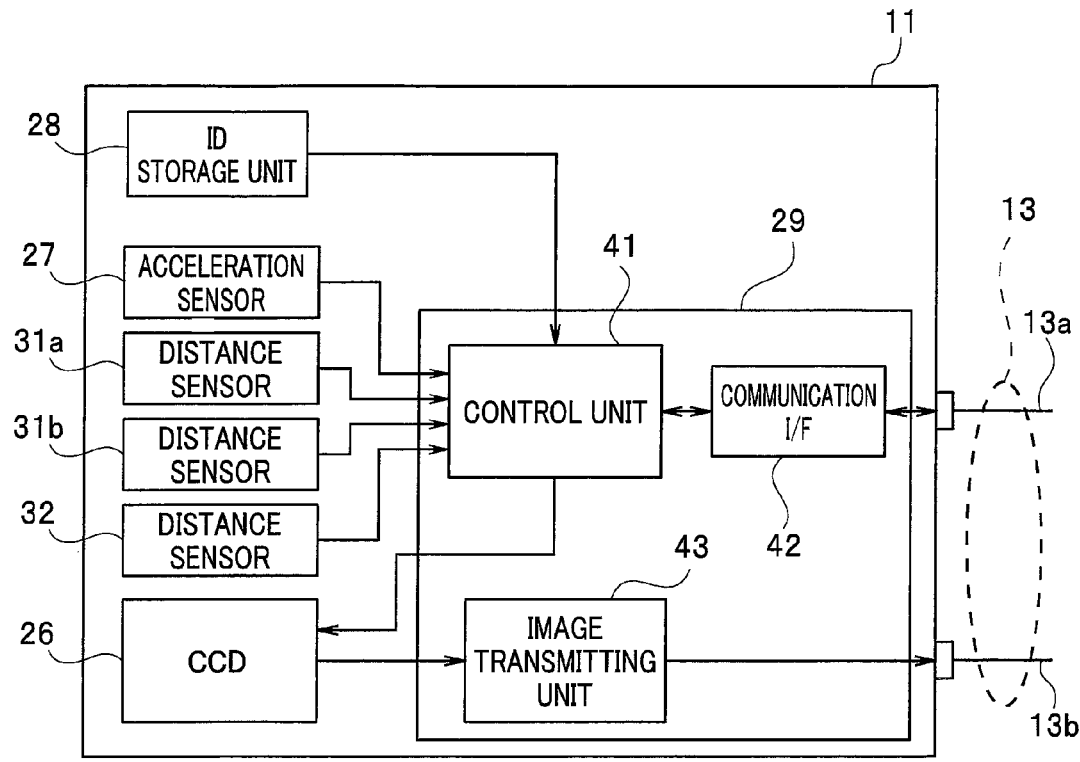
FIG. 3 is a block diagram showing the circuit configuration of the borescope 11 according to the first embodiment.

FIG. 3 is a block diagram showing the circuit configuration of the borescope 11. The communication control unit 29 includes a control unit 41, a communication interface unit (hereinafter referred to as "communication I/F") 42 connected to a signal line 13a in the cable 13 for the purpose of communicating with the PC 12, and an image transmitting unit 43 connected to a signal line 13b for transmitting the image signal from the CCD 26 to the PC 12. The communication I/F 42 is connected to the control unit 41 and to the signal line 13a in the cable 13 connected to the PC 12.

The control unit 41 includes a central processing unit (CPU), a ROM and a RAM, is supplied with output signals from the various sensors, executes a predetermined calculation process and outputs predetermined sorts of information to the PC 12 through the communication I/F 42.

The CCD 26, the acceleration sensor 27, the ID storage unit 28 and the distance sensors 31a, 31b, and 32 are connected to the control unit 41.

The control unit 41 is supplied with the scope ID for the borescope 11 from the ID storage unit 28 and is also supplied with detection signals from the acceleration sensor 27 and the distance sensors 31a, 31b, and 32.

The control unit 41 supplies a drive signal to the CCD 26 to drive the CCD 26.

The control unit 41 calculates the insertion length L based on the distance d3 corresponding to the detection signal from the distance sensor 32.

The insertion length L is the distance from a pivot point Ph, which is assumed to correspond to a center of the insertion hole in the fixing portion F, as shown in FIG. 2, and on which the distal end portion of the insertion section 11a is moved in a direction perpendicular to the axial direction, to an image pickup optical center Pc when an image of an object is picked up through the observation window 15.

The pivot point Ph in the fixing implement F is determined in advance from the shape of the fixing implement F and the shape of the insertion section 11a. The positional relationship between the distance sensor 32 and the image pickup optical center Pc is also determined in advance. Therefore, even when the insertion section 11a is moved along the axial direction, the control unit 41 can calculate the insertion amount L from the distance d3 corresponding to the detection output signal from the distance sensor 32.

Note that the insertion length L may be determined with reference to points other than the pivot point Ph and the image pickup optical center Pc.

The control unit 41 also calculates, as attitude information about the borescope 11, based on detection signals from the acceleration sensor 27, the angle of elevation β, which is an inclination of the borescope 11 from the direction of gravity g, and the angle of rotation γ of the borescope 11 about the axis.

The acceleration sensor 27 outputs three detection signals with respect to the direction of gravity g. Normalization processing is performed on the three outputted detection signals, and the angle of elevation β and the angle of rotation γ are calculated based on the three detection signals thereby normalized. If three values Dx, Dy, and Dz are obtained by normalizing the three detection signals from the acceleration sensor 27, the angle of elevation β is $\cos^{-1}(-Dz)$ and the angle of rotation γ is $\tan^{-1}(-Dy/Dx)$. Accordingly, the acceleration sensor 27 is provided in the borescope 11 to constitute an attitude detection unit that detects the attitude of the insertion section 11a. The attitude is defined with the angle of elevation β, which is an inclination of the insertion section 11a from a predetermined direction, and the angle of rotation γ about the axis of the insertion section 11a.

The control unit 41 calculates the distances d1 and d2 as two distance information items based on the values of the detection signals from the two distance sensors 31a and 31b, respectively.

The control unit 41 outputs, to the PC 12, in real time, through the communication I/F 42, the insertion length L, attitude information and distance information calculated based on the detection signals from the respective sensors.

The image signal outputted from the CCD 26 is converted into a digital signal in the image transmitting unit 43 and is outputted from the signal line 13b in the cable 13. The image transmitting unit 43 outputs the digital image signal in a differential signal format such as LVDS to the signal line 13.

(Configuration of PC)

Figure 4:
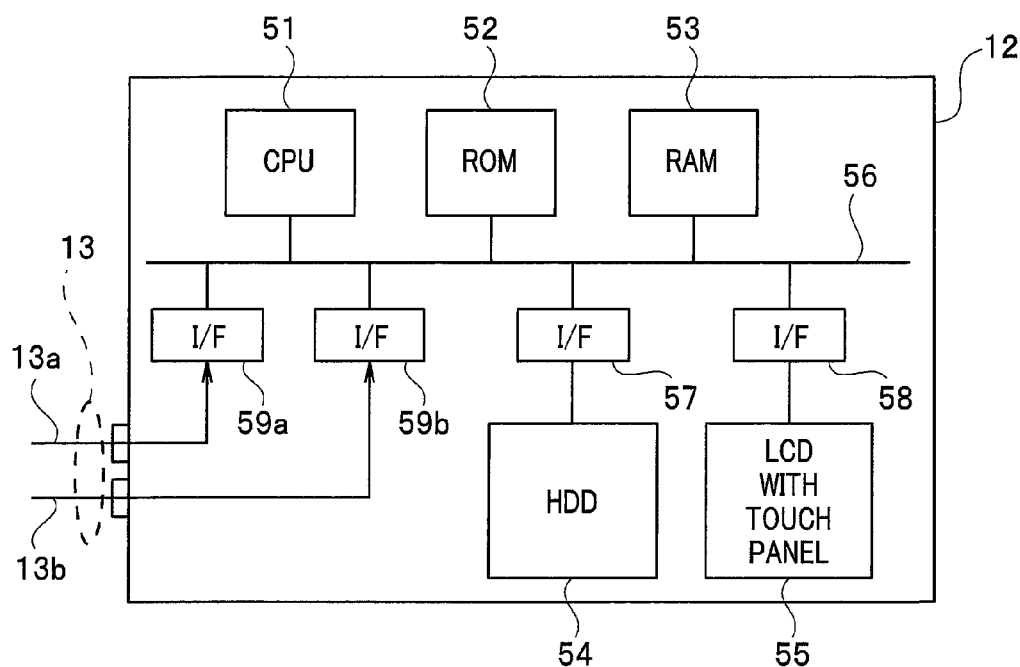
FIG. 4 is a block diagram showing the configuration of a PC 12 according to the first embodiment.

FIG. 4 is a block diagram showing the configuration of the PC 12. The PC 12 includes a central processing unit (hereinafter referred to as "CPU") 51, a ROM 52, a RAM 53, a hard disk drive (hereinafter referred to as "HDD") 54 and a liquid crystal display (hereinafter referred to as "LCD") 55. The CPU 51, the ROM 52 and the RAM 53 are connected to each other by a bus 56. The HDD 54 and the LCD 55 are connected to the bus 56 through interfaces (hereinafter referred to as "I/F") 57 and 58, respectively.

The LCD 55 is a display with a touch panel. The CPU 51 can cause the LCD 55 to display an endoscopic image, a predetermined menu view, a GUI view described below, and the like and can detect a command input from a user by receiving an output signal from the touch panel.

The PC 12 further has I/Fs 59a and 59b to which the signal lines 13a and 13b in the cable 13 are respectively connected. The PC 12 communicates with the control unit 41 through the I/F 59a, and receives image signals from the borescope 11 through the IN 59b. A user can display as inspection image an image signal from the borescope 11 on the screen of the LCD 55 and can record the image signal in the HDD 54.

When an inspection image is recorded, the predetermined sorts of information obtained from the detection signals from the respective sensors or calculated with respect to the inspection image to be recorded are recorded together with the inspection image in the HDD 54. Accordingly, the HDD 54 constitutes a storage unit that stores the insertion length L of the insertion section 11a detected with the distance sensor 32 when a still image of a blade B picked up with the borescope 11 is obtained, the attitude of the insertion section 11a detected with the acceleration sensor 27, and the two distances from the insertion section 11a detected with the two distance sensors 31a and 31b. In the present embodiment, information including the insertion length L is recorded in image data on the inspection image as EXIF information for the image data, and the image data is stored in the HDD 54.

When the borescope 11 is connected to the PC 12 through the cable 13, the control unit 41 in the borescope 11 transmits the scope ID stored in the ID storage unit 28 to the PC 12 and to the CPU 51. The PC 12 can thus obtain the scope ID for the borescope 11.

The PC 12 can then obtain information on the insertion length, the attitude and the distances in real time from the borescope 11 through the communication I/F 59.

(Procedure of Inspection)

A user as an inspector who inspects blades first performs an overall inspection of the blades by using a borescope of a wide view angle. The user thereafter performs a detailed inspection by using a borescope of a narrow view angle and by displaying an enlarged image of a defective portion found in the preceding inspection.

Figure 5:
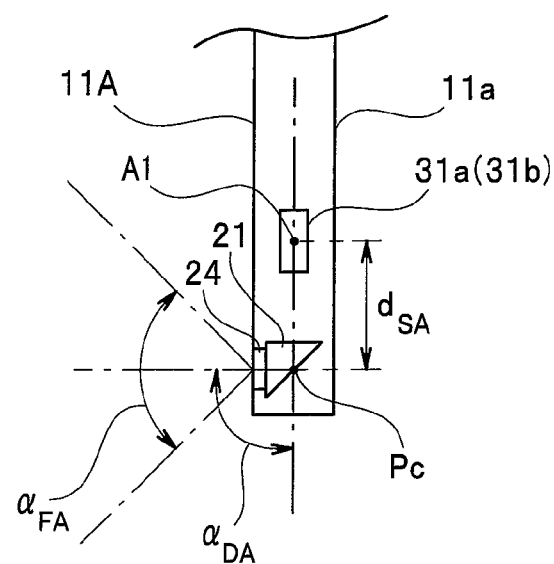
FIG. 5 is a diagram for explaining the view angle of a borescope 11A, which is comparatively wide, according to the first embodiment.
Figure 6:
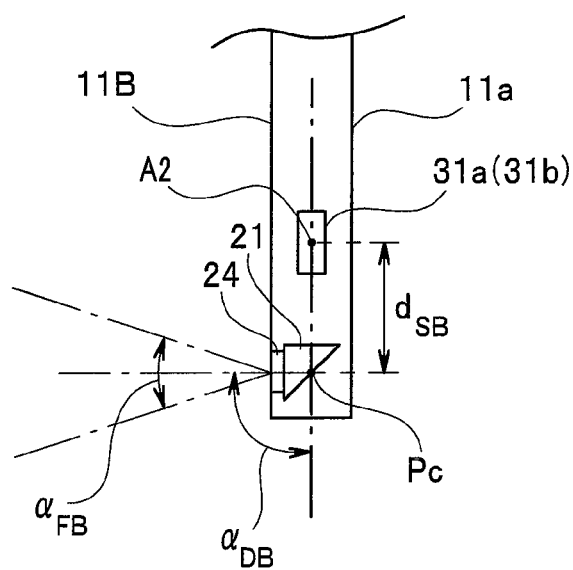
FIG. 6 is a diagram for explaining the view angle of a borescope 11B, which is narrower than that of the borescope 11A shown in FIG. 5, according to the first embodiment.
Figure 7:
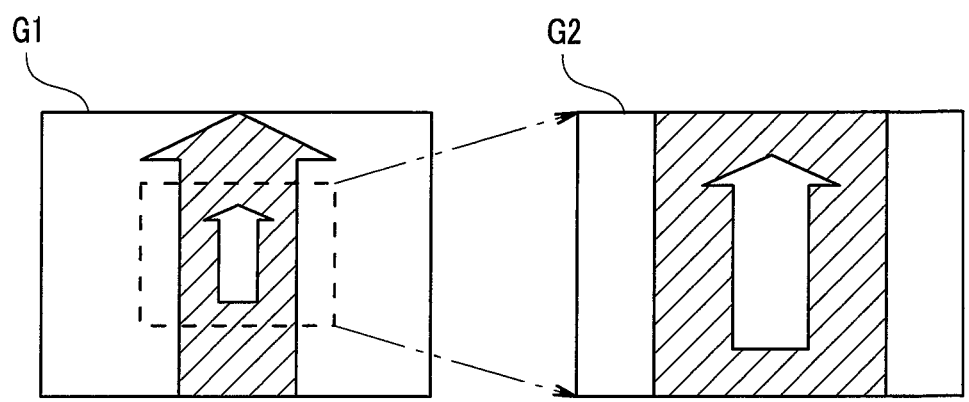
FIG. 7 is a schematic explanatory diagram for explaining the difference between endoscopic images picked up with the two borescopes differing in view angle according to the first embodiment.

FIGS. 5 and 6 are diagrams for explaining the difference in view angle between borescopes. FIG. 5 is a diagram for explaining the view angle of a borescope 11A, which is a comparatively wide. FIG. 6 is a diagram for explaining the view angle of a borescope 11B, which is narrower than that of the borescope 11A shown in FIG. 5. FIG. 7 is a schematic explanatory diagram for explaining the difference between endoscopic images picked up with the two borescopes differing in view angle.

Common details and the difference between the borescopes 11A and 11B will be described. The borescopes 11A and 11B are identical in external shape and size to each other. Also, as shown in FIGS. 5 and 6, distances $d_{SA}$ and $d_{SB}$ from the image pickup optical centers Pc passing through the optical axis centers of the mirrors 21 to axes A1 and A2 passing through two central positions in the two distance sensors 31a and 31b in the optical systems, as seen in side views of the borescopes 11A and 11B along the axes A1 and A2 passing through the two central positions in the two distance sensors 31a and 31b, are equal to each other. That is, the distance $d_{SA}$ from the image pickup optical center Pc of the mirror 21 to the axis A1 passing through the central positions in the two distance sensors 31a and 31b in the optical system of the borescope 11A is equal to the distance $d_{SB}$ from the image pickup optical center Pc to the axis A2 passing through the center positions in the distance sensors 31a and 31b in the borescope 11B.

The view angle $\alpha_{FA}$ of the borescope 11A shown in FIG. 5 is determined by the objective optical system 22, the relay optical system 23 and the image pickup optical system 25 in the borescope 11A. Similarly, the view angle $\alpha_{FB}$ of the borescope 11B shown in FIG. 6 is determined by the objective optical system 22, the relay optical system 23 and the image pickup optical system 25 in the borescope 11B. The view angle $\alpha_{FA}$ is larger than the view angle $\alpha_{FB}$.

Further, as shown in FIGS. 5 and 6, a viewing direction angle $\alpha_{DA}$ from the axial direction of the insertion section 11a of the borescope 11A is equal to a viewing direction angle $\alpha_{DB}$ from the axial direction of the insertion section 11a of the borescope 11B. Note that each of the viewing direction angle $\alpha_{DA}$ and the viewing direction angle $\alpha_{DB}$ in the present embodiment is 90 degrees.

That is, the borescope 11A has the insertion section 11a, the distance sensor that detects the same insertion length L as that detected by the distance sensor 32 of the borescope 11B, the acceleration sensor that detects the same attitude as that detected by the acceleration sensor 27 of the borescope 11B, and the two distance sensors 31a and 31b that detect the same two distances d1 and d2 as the borescope 11B.

As described above, the respective parameters of the two borescopes 11A and 11B other than the view angles in the image pickup optical systems are equal to each other. Therefore, the image pickup optical centers Pc the two borescopes 11A and 11B in image pickup from an object coincide with each other when the borescopes 11A and 11B have the same insertion amount L and the same viewing direction.

Referring to FIG. 7, an inspection image G1 is an image picked up with the borescope 11A, and an inspection image G2 is an image picked up with the borescope 11B. Since the view angle $\alpha_{FB}$ of the borescope 11B is smaller than the view angle $\alpha_{FA}$ of the borescope 11A, the inspection image G2 is an enlarged image corresponding to a central portion of the inspection image G1. In the endoscopic image G2 shown in FIG. 7, a blank arrow in the inspection image G1 is enlarged.

If the insertion lengths of the insertion section 11a of the borescope 11A and the insertion section 11a of the borescope 11B are equal to each other, and if the directions from the image pickup optical centers Ps toward the object coincide with each other, the central-portion images in the inspection images G1 and G2 are images picked up from the same position on the blade B, as shown in FIG. 7.

The blade inspection system 1 assists the user in operating the borescope 11B so that after the user as an inspector has first observed and inspected the blade B with the borescope 11A, the user can observe and inspect, by using the borescope 11B having a narrower view angle, and by enlarging the image of the blade B, a defective portion found by inspection with the borescope 11A.

(Function)

The operation of the blade inspection system 1 will be described.

Figure 8:
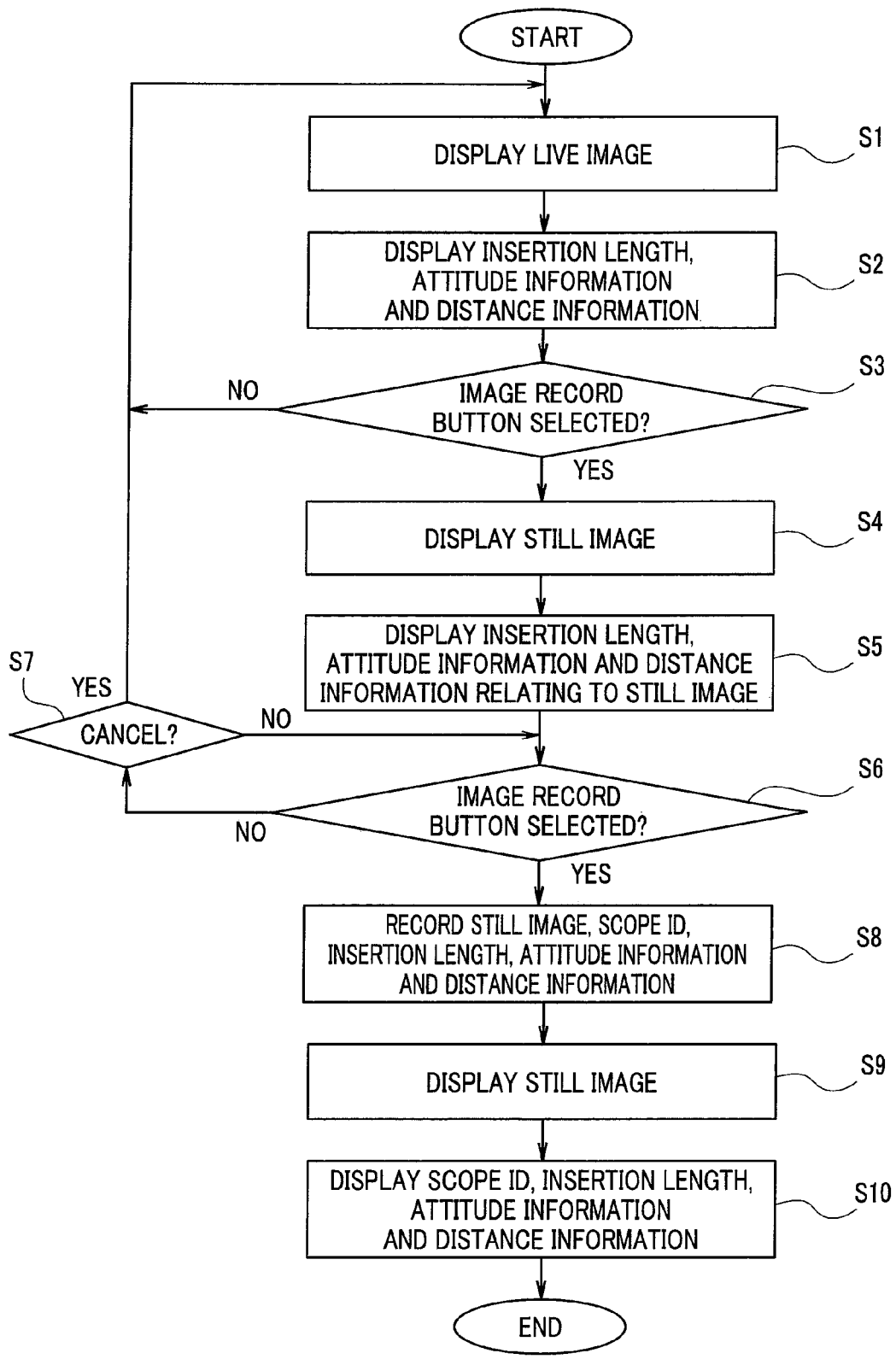
FIG. 8 is a flowchart showing an example of a flow of recording processing according to the first embodiment when the borescope 11 is inserted and an endoscopic image is displayed and recorded.
Figure 9:
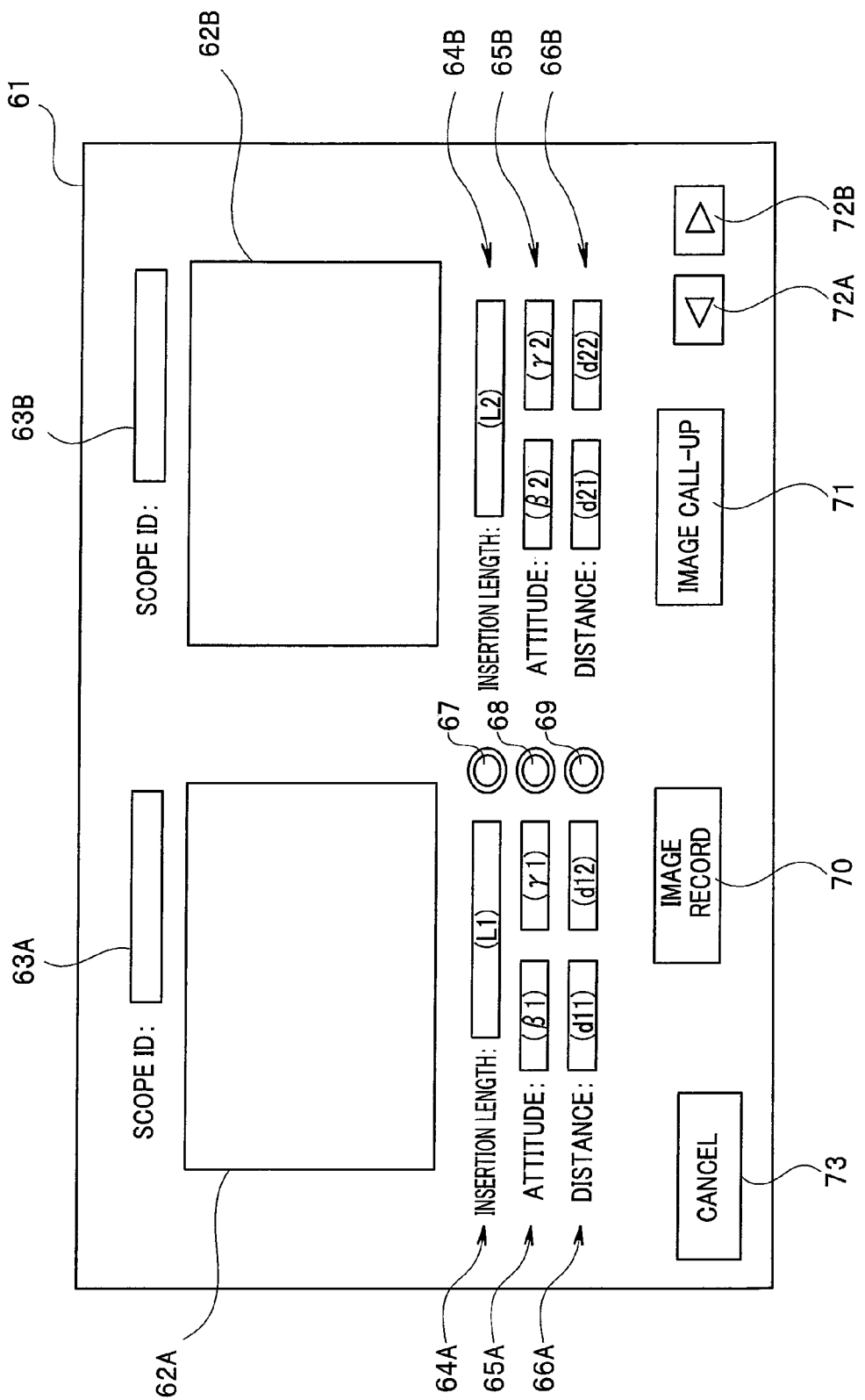
FIG. 9 is a diagram showing an example of a graphical user interface (GUI) displayed on the screen of an LCD 55 of the PC 12 according to the first embodiment.

FIG. 8 is a flowchart showing an example of a flow of recording processing when the borescope 11 is inserted and an endoscopic image is displayed and recorded. A program for recording processing shown in FIG. 8 is stored in the ROM 52 in the PC 12 and is read out and executed by the CPU 51. FIG. 9 is a diagram showing an example of a graphical user interface (GUI) displayed on the screen of the LCD 55 of the PC 12.

The configuration of the GUI (graphical user interface) displayed on the screen of the LCD 55 of the PC 12 at the time of blade inspection will first be described with reference to FIG. 9.

As shown in FIG. 9, a GUI 61 displayed on the screen of the LCD 55 of the PC 12 is a graphical user interface including two image display portions 62A and 62B in which inspection images are displayed, a scope ID display portions 63A and 63B in which scope IDs are displayed, two insertion length information display portions 64A and 64B in which insertion lengths are displayed, two attitude information display portions 65A and 65B in which attitude information is displayed, and two distance information display portions 66A and 66B in which distance information is displayed.

The GUI 61 further includes match indicators 67, 68, and 69 each of which indicates a match between information items in one of three sorts of information, an image record button 70, an image call-up button 71, a backward button 72A, a forward button 72B, and a cancel button 73.

The image display portion 62A is a display area in which a live inspection image in current inspection received from the borescope 11 is displayed. The image display portion 62B is a display area in which a still image from inspection images recorded in the HDD 54 provided as a storage unit is displayed.

The scope ID display portions 63A and 63B are each a display area in which the scope ID for the borescope 11 when the corresponding one of inspection images displayed in the image display portions 62A and 62B is being obtained or was obtained is displayed.

The insertion length information display portions 64A and 64B are each a display areas in which the insertion length L of the borescope 11 determined when the corresponding one of inspection images displayed in the image display portions 62A and 62B is being obtained or was obtained is displayed. The insertion length L is a value calculated and transmitted by the control unit 41 in the borescope 11 based on the output from the distance sensor 32. In the insertion length information display portion 64A, the insertion length L1 determined when an inspection image displayed in the image display portion 62A is being obtained or was obtained is displayed. In the insertion length information display portion 64B, the insertion length L2 determined when an inspection image displayed in the image display portion 62B was obtained is displayed.

The attitude information display portions 65A and 65B are each a display area in which attitude information about the borescope 11 produced when the corresponding one of inspection images respectively displayed in the image display portions 62A and 62B was obtained is displayed. The attribute information includes the angle of elevation β which is an inclination of the borescope 11 from the direction of gravity g and the angle of rotation γ about the axis, which angles are calculated from the outputs from the acceleration sensor 27. The attitude information display portion 65A has two display areas in which the angle of elevation β1 and the angle of rotation γ1 determined when an inspection image displayed in the image display portion 62A is being obtained or was obtained are displayed. The attitude information display portion 65B also has two display areas in which the angle of elevation β2 and the angle of rotation γ2 determined when an inspection image displayed in the image display portion 62B was obtained are displayed.

The distance information display portions 66A and 66B are each a display area in which distance information obtained from the outputs from the two distance sensors 31a and 31b of the borescope 11 when the corresponding one of inspection images displayed in the image display portions 62A and 62B was obtained is displayed. The distance information is two distances d1 and d2 calculated and transmitted by the control unit 41 based on the outputs from the two distance sensors 31a and 31b. The distance information display portion 66A has two display areas in which two distances d11 and d12 determined when an inspection image displayed in the image display portion 62A is being obtained or was obtained are displayed. The distance information display portion 66B has two display areas in which two distances d21 and d22 determined when an inspection image displayed in the image display portion 62B was obtained are displayed. The distances d11 and d21 correspond to the distance d1 in FIG. 2, and the distances d21 and d22 correspond to the distance d2 in FIG. 2.

The match indicator 67 is a display portion that indicates a match between the insertion length determined when an inspection image in still image form displayed in the image display portion 62B was obtained and the insertion length relating to a live inspection image displayed in the image display portion 62A, as described below. A match between the two insertion lengths with an error within a predetermined error range is indicated, for example, by changing the luminance or the color of the match indicator 67. Accordingly, a match between the two insertion lengths implicates not only a perfect match between the two insertion lengths but also a match with an error within the predetermined error range.

In the present embodiment, the match indicator 67 indicates, when red in color, that there is no match between the insertion length relating to a still image and the insertion length relating to a live image. When green in color, the match indicator 67 indicates that there is a match between the insertion length relating to a still image and the insertion length relating to a live image.

The match indicator 68 is a display portion that indicates a match between attitude information produced when an inspection image in still image form displayed in the image display portion 62B was obtained and attitude information about a live inspection image displayed in the image display portion 62A, as described below. A match between the two groups of attitude information with an error within a predetermined error range is indicated, for example, by changing the luminance or the color of the match indicator 68. Accordingly, a match between the two groups of attitude information implicates not only a perfect match between the two groups of attitude information but also a match with an error within the predetermined error range. Also, the match indicator 68 indicates, when red in color, that there is no match between the attitude relating to a still image and the attitude relating to a live image. When green in color, the match indicator 68 indicates that there is a match between the attitude relating to a still image and the attitude relating to a live image.

The match indicator 69 is a display portion that indicates a match between distance information produced when an inspection image in still image form displayed in the image display portion 62B was obtained and distance information about a live inspection image displayed in the image display portion 62A, as described below. A match between the two groups of distance information with an error within a predetermined error range is indicated, for example, by changing the luminance or the color of the match indicator 69. Accordingly, a match between the two groups of distance information implicates not only a perfect match between the two groups of distance information but also a match with an error within the predetermined error range. Also, the match indicator 69 indicates, when red in color, that there is no match between distance information about a still image and distance information about a live image. When green in color, the match indicator 69 indicates that there is a match between distance information relating to a still image and distance information relating to a live image.

Note that the match indicator 67 may be not changed from red to green when a match occurs between the insertion length relating to a live inspection image and the insertion length determined when an inspection image in still image form displayed in the image display portion 62B was obtained; the match indicator 67 may be changed to a predetermined color, for example, yellow when the insertion length relating to a live inspection image enters a predetermined distance range with respect to the insertion length determined when an inspection image in still image form displayed in the image display portion 62B was obtained, and may be thereafter changed to green when a match occurs therebetween.

The colors of the other match indicators 68 and 69 may also be changed in a similar way. The color of the match indicator 68 or 69 may be changed to a predetermined color, e.g., yellow when attitude information or distance information about a live inspection image enters a predetermined value range with respect to attitude information or distance information produced when an inspection image in still image form was obtained, and may be thereafter changed to green when a match occurs therebetween.

The image record button 70 is a button displayed on the LCD 55 and operated by being touched by a user when a still image from a live image displayed in the image display portion 62A is to be recorded, as described below.

The image call-up button 71 is a button displayed on the LCD 55 and operated by being touched by a user when a still image recorded in the HDD 54 is called up and displayed in the image display portion 62B, as described below.

The backward button 72A is a button displayed on the LCD 55 and operated, when a plurality still images that are recorded in the HDD 54 are called up, to display the still image in the image display portion 62B by scrolling back from one image to another in predetermined order, as described below.

The forward button 72B is a button displayed on the LCD 55 and operated, when a plurality still images that are recorded in the HDD 54 are called up, to display the still image in the image display portion 62B by scrolling forward from one image to another in predetermined order, as described below.

The cancel button 73 is a button used by a user as an inspector when the user cancels a command after selecting the command.

The GUI 61 shown in FIG. 9 is displayed on the LCD 55 of the PC 12, and a user inspects the blade B.

As shown in FIG. 8, the CPU 51 displays on the LCD 55 a live inspection image (hereinafter referred to as "live image"), which is a moving endoscopic image, based on the image signal received from the borescope 11 (S1). The live image is displayed in the image display portion 62A of the GUI 61. At this time, since the scope ID is also received from the control unit 41 in the borescope 11, the CPU 51 displays the scope ID in the scope ID display portion 63A.

The CPU 51 then displays, in the insertion length information display portion 64A, the attitude information display portion 65A and the distance information display portion 66A, respectively, the insertion length, attitude information and position information received in real time (S2).

The CPU 51 determines whether or not the image record button 70 has been selected or touched (S3). If the image record button 70 has not been selected (S3: NO), the process returns to S1.

If the image record button 70 has been selected (S3: YES), the CPU 51 produces a still image from the received live image and displays the still image in the image display portion 62A (S4).

The CPU 51 then displays, in the insertion length information display portion 64A, the attitude information display portion 65A and the distance information display portion 66A, respectively, the insertion length, attitude information and position information produced when the still image displayed in the image display portion 62A was obtained (S5).

The CPU 51 determines whether or not the image record button 70 has been again selected or touched (S6). If the image record button 70 has not been selected (S6: NO), the CPU 51 determines whether or not the cancel button 73 has been selected (S7). If the cancel button 73 has been selected (S7: YES), the process returns to S1. If the cancel button 73 has not been selected, no processing is performed.

If the image record button 70 has been selected (S6: YES), the CPU 51 records, in the HDD 54 provided as a storage device, the still image displayed in the image display portion 62A, the scope ID, and the insertion length, the attitude information and the position information relating to the still image (S8). The scope ID, the insertion length, the attitude information and the position information are included as EXIF information for image data in the image data and recorded in the HDD 54.

The CPU 51 displays the recorded still image in the image display portion 62B (S9), and displays, in the scope ID display portion 63B, the insertion length information display portion 64B, the attitude information display portion 65B and the distance information display portion 66B, respectively, the scope ID, the insertion length, the attitude information and the position information when the still image displayed in the image display portion 62B was obtained (S10).

The user can thus record a still image from an inspection image of the blade B in the engine E. The user can store a plurality of inspection images in the HDD 54 as a result of repeated execution of the process shown in FIG. 8.

For example, the process shown in FIG. 8 is performed by using the borescope 11A having a comparatively wide view angle to roughly inspect the blade B, and a still image containing an image of a flawed portion is first recorded. To observe or record by enlarging the flawed portion, the inspector draws out the borescope 11A from the access port AP and inserts through the access port AP the borescope 11B having a view angle narrower than that of the borescope 11A.

Figure 10:
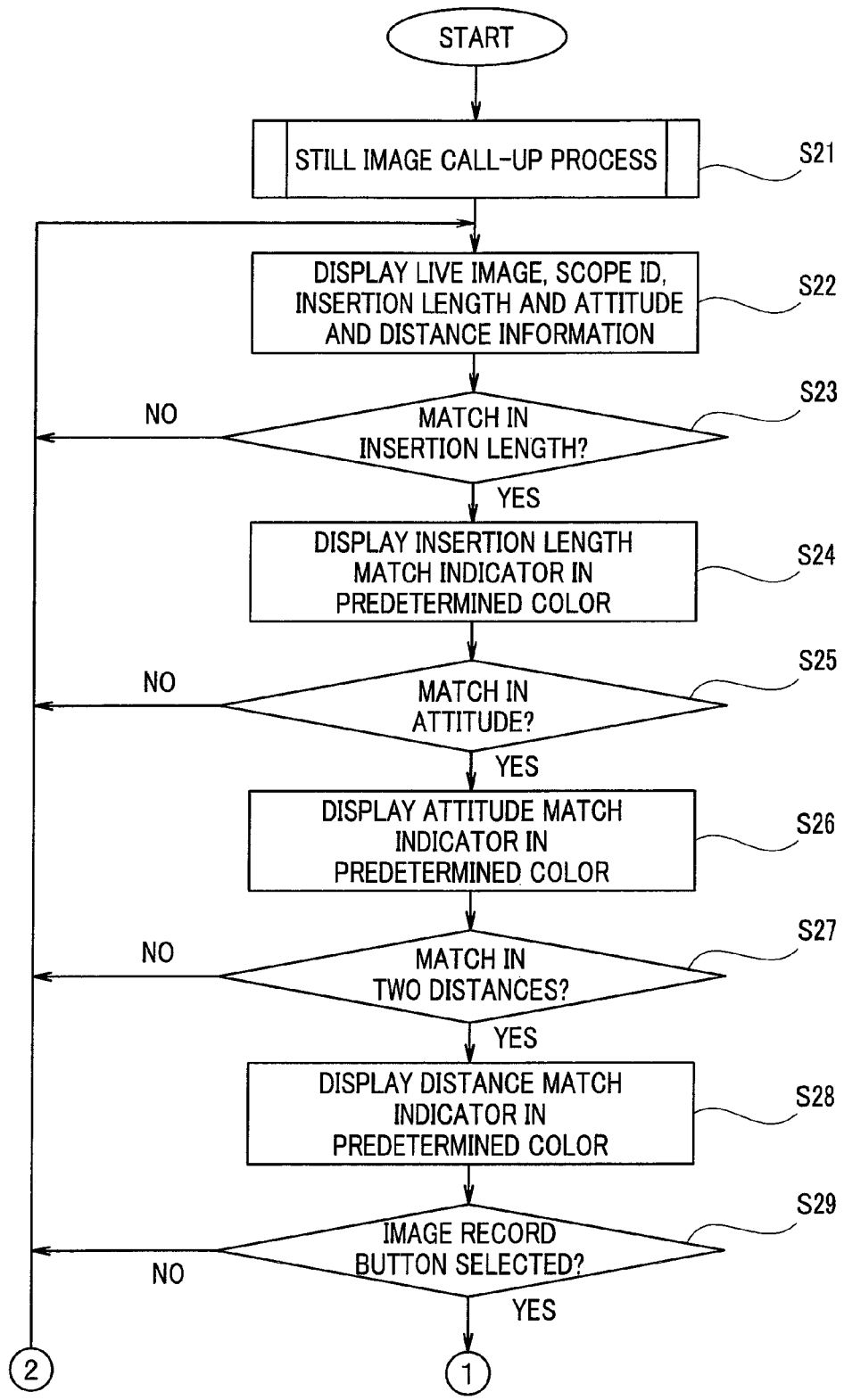
FIG. 10 is a flowchart showing an example of a flow of recording processing according to the first embodiment when a borescope 11 having a narrower view angle is inserted and an inspection image is displayed and recorded while referring to a recorded inspection image.
Figure 11:
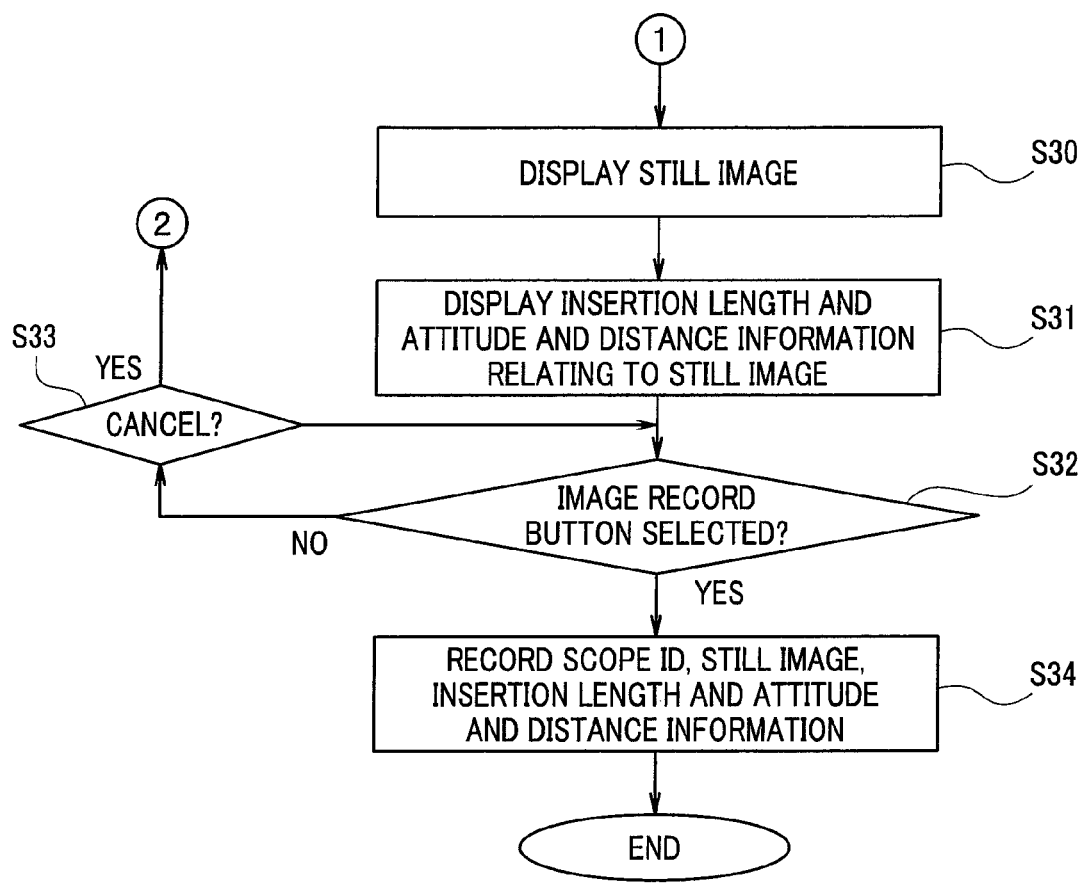
FIG. 11 is a flowchart showing an example of a flow of recording processing according to the first embodiment when a borescope 11 having a narrower view angle is inserted and an inspection image is displayed and recorded while referring to a recorded inspection image.

FIGS. 10 and 11 are flowcharts showing an example of a flow of recording processing for displaying and recording inspection images while inserting the borescope 11 having a narrower view angle and referring to recorded inspection images. A program for the recording process shown in FIGS. 10 and 11 is stored in the ROM 52 and is read out and executed by the CPU 51 in the PC 12.

When the image call-up button 71 of the GUI 61 is selected or touched by the inspector, the process shown in FIGS. 10 and 11 is executed.

The CPU 51 first executes an image call-up process (S21). A first inspection image, e.g., the earliest in the past in a time series from the plurality of inspection images recorded in the HDD 54 is displayed in the image display portion 62B. The user can select a desirable one of the plurality of inspection images recorded in the HDD 54 and display the selected inspection image in the image display portion 62B by using the forward button 72B and the backward button 72A.

When the inspection image selected by the user is displayed in the image display portion 62B, the scope ID, the insertion length, the attitude information and the position information relating to the inspection image are displayed in the scope ID display portion 63B, the insertion length information display portion 64B, the attitude information display portion 65B and the distance information display portion 66B, respectively.

The user can thus display the recorded inspection image and the scope ID, the insertion length, the attitude information and the position information relating to the recorded inspection image in the GUI 61.

While the user inserts the borescope 11B in the engine E, the CPU 51 displays in the scope ID display portion 63A the scope ID received from the borescope 11B, displays a live image in the image display portion 62A, and displays the insertion length, attitude information and position information relating to the live image in the insertion length information display portion 64A, the attitude information display portion 65A and the distance information display portion 66A, respectively, in real time (S22). When the borescope 11B is moved, not only the live image displayed in the display portion 62A but also the display contents in the insertion length information display portion 64A, the attitude information display portion 65A and the distance information display portion 66A are changed in real time.

At this time, the CPU 51 determines whether there is a match between the insertion length L2 determined when the inspection image in still image form displayed in the image display portion 62B was obtained and the insertion length L1 of the borescope 11B with which the current live image is being obtained (S23). If there is no match therebetween (S23: NO), the process returns to S22. Processing in S23 constitutes an insertion length comparison section that makes a comparison between the insertion length L1 detected by the distance sensor 32 of the borescope 11B and the insertion length L2 relating to the inspection image stored in HDD 54 and displayed in the image display portion 62B.

That is, in the user's operation to insert the borescope 11B so that the borescope 11B advances toward an inner portion of the engine E, the user inserts the borescope 11B in the engine E while checking whether or not the match indicator 67 is changed from red to green, and stops the inserting operation when the match indicator 67 is changed from red to green.

Note that in determination in S23 as to whether or not there is a match between the two insertion lengths, it is determined that there is a match between the two insertion lengths if the insertion length L1 of the borescope 11B with which the current live image is being obtained falls within a predetermined allowable range with respect to the insertion length L2. For example, if the insertion length L1 is within a range from (L2−Δk1) to (L2+Δk1), it is determined that there is a match between the two insertion lengths.

If there is a match between the two insertion lengths (S23: YES), the CPU 51 gives the match indicator 67 an indication in a predetermined color, green in the present embodiment (S24). When the color of the match indicator 67 is changed to green, the user can recognize the match between the insertion length L2 determined when the inspection image displayed in the image display portion 62B was obtained and the insertion length L1 of the borescope 11B with which the current live image is being obtained. Thus, processing in S24 constitutes a match output section that outputs match information indicating that there is a match between the insertion length L1 detected by the distance sensor 32 of the borescope 11B and the insertion length L2 relating to the inspection image stored in the HDD 54 and displayed in the image display portion 62B. With the output of the predetermined match information as a result of processing in S24, the indication (color in the present embodiment) with the match indicator 67, which is a predetermined mark displayed on the LCD 55 provided as a display device, is changed.

Next, the user changes the attitude of the borescope 11B while holding the borescope 11B so that the insertion length L1 of the borescope 11B is not changed. The user changes the attitude of the borescope 11B while checking whether or not the match indicator 68 is changed from red to green, and stops the attitude changing operation when the match indicator 68 is changed from red to green.

The CPU 51 therefore determines whether there is a match between the attitude determined when the inspection image in still image form displayed in the image display portion 62B was obtained and the attitude of the borescope 11B with which the current live image is being obtained (S25). "A match between the attitudes" refers to a match both in angle of elevation and in angle of rotation.

If there is no match between the two attitudes (S25: NO), the process returns to S22. Processing in S25 constitutes an attitude comparison section that makes a comparison between the attitude (the angle of elevation $\beta$ and the angle of rotation $\gamma$ in the present embodiment) detected by the acceleration sensor 27 of the borescope 11B and the attitude (the angle of elevation $\beta$ and the angle of rotation $\gamma$ in the present embodiment) relating to the inspection image stored in the HDD 54 and displayed in the image display portion 62B.

Note that in determination in S25 as to whether or not there is a match between the two attitudes, it is determined that there is a match between the two attitudes if the angle of elevation $\beta$ and the angle of rotation $\gamma$ calculated from the outputs from the acceleration sensor 27 of the borescope 11B with which the current live image is being obtained fall within predetermined allowable ranges with respect to the angle of elevation $\beta$ and the angle of rotation $\gamma$ calculated from the outputs from the acceleration sensor 27 with respect to the inspection image displayed in the image display portion 62B. For example, if the angle of elevation $\beta 1$ of the borescope 11B is within a range from ($\beta 2-\Delta k2$) to ($\beta 2+\Delta k2$) with respect to the borescope 11A, and if the angle of rotation $\gamma 1$ of the borescope 11B is within a range from ($\gamma 2-\Delta k3$) to ($\gamma 2+\Delta k3$) with respect to the borescope 11A, it is determined that there is a match between the two attitudes.

If there is a match between the two attitudes (S25: YES), the CPU 51 gives the match indicator 68 an indication in a predetermined color, green in the present embodiment (S26). When the color of the match indicator 68 is green, the user recognizes the match between the attitude determined when the inspection image displayed in the image display portion 62B was obtained and the attitude of the borescope 11B with which the current live image is being obtained.

Thus, processing in S26 constitutes a match output section that outputs match information indicating that there is a match between the attitude (the angle of elevation $\beta$ and the angle of rotation $\gamma$ in the present embodiment) detected by the acceleration sensor 27 of the borescope 11B and the attitude (the angle of elevation $\beta$ and the angle of rotation $\gamma$ in the present embodiment) relating to the inspection image stored in the HDD 54 and displayed in the image display portion 62B. With the output of the predetermined match information as a result of processing in S26, the indication (color in the present embodiment) with the match indicator 68, which is a predetermined mark displayed on the LCD 55 provided as a display device, is changed.

Next, the user changes the position of the distal end portion of the insertion section 11a of the borescope 11B while holding the borescope 11B so that the insertion length L1 and the attitude (the angle of elevation $\beta 1$ and the angle of rotation $\gamma 1$) of the borescope 11B are not changed. The user changes the position of the borescope 11B while checking whether or not the match indicator 69 is changed from red to green, and stops the position changing operation when the match indicator 69 is changed from red to green.

The CPU 51 therefore determines whether there is a match between the two distances d1 and d2 determined when the inspection image in still image form displayed in the image display portion 62B was obtained and the two distances d1 and d2 of the borescope 11B with which the current live image is being obtained (S27).

If there is a match between the two groups of the distances (S27: YES), there is a match between the position of the image pickup optical center Pc of the insertion section 11a of the borescope 11A determined when the inspection image displayed in the image display portion 62B was obtained and the position of the image pickup optical center Pc of the borescope 11B with which the current live image is being obtained.

Processing in S27 constitutes a distance comparison section that makes a comparison between the two distances d1 and d2 detected by the two distance sensors 31a and 31b of the borescope 11B and the two distances d1 and d2 relating to the inspection image stored in the HDD 54 and displayed in the image display portion 62B.

The position of the distal end portion of the insertion section 11a will be described below.

Figure 13:
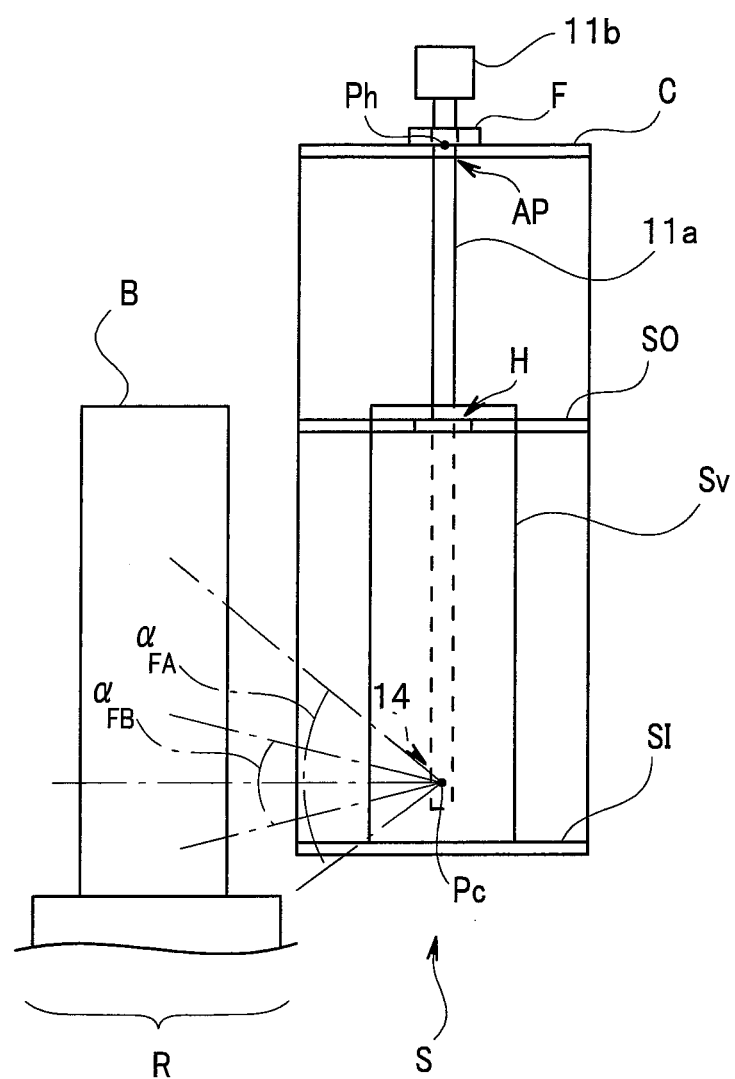
FIG. 13 is diagram for explaining the state of the insertion section 11a according to the first embodiment when one stator vane Sv is seen along a direction perpendicular to an axis of rotation Ax of a rotor in explanation of a state where the insertion section 11a is inserted in the casing C of the engine E.
Figure 14:
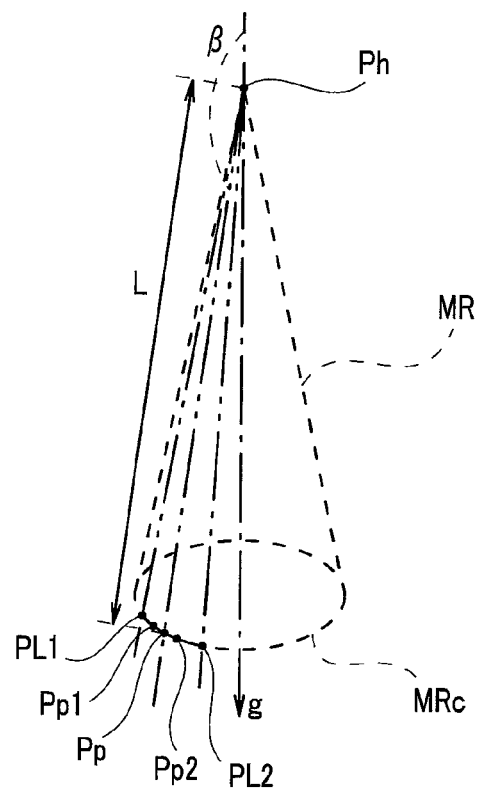
FIG. 14 is a schematic diagram for explaining a movable region MR for the insertion section 11a according to the first embodiment.
Figure 15:
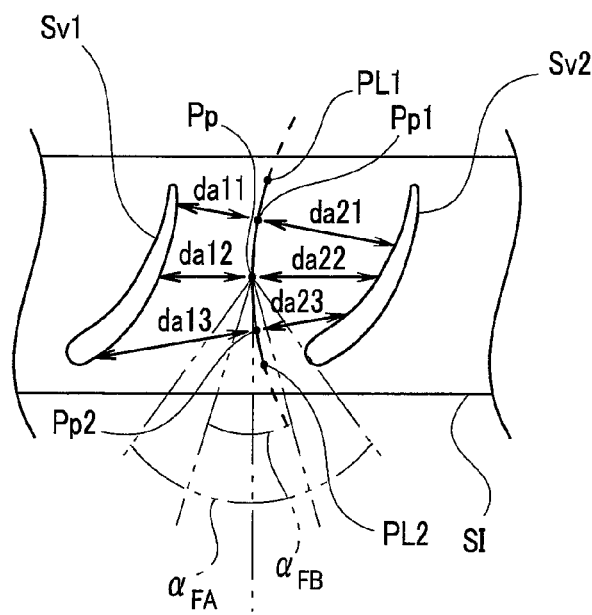
FIG. 15 is a schematic diagram for explaining a position change region for the image pickup optical center of a distal end portion of the insertion section 11a according to the first embodiment.

FIGS. 12 to 15 are diagrams for explaining the position of the distal end portion of the insertion section 11a. FIG. 12 is a perspective view of a portion of the stator S for explaining a state where the insertion section 11a is inserted in the casing C of the engine E. FIG. 13 is a diagram for explaining the state of the insertion section 11a when one stator vane Sv is seen along a direction perpendicular to the axis of rotation Ax of the rotor in explanation of a state where the insertion section 11a is inserted in the casing C of the engine E. FIG. 14 is a schematic diagram for explaining a movable region MR for the insertion section 11a. FIG. 15 is a schematic diagram for explaining a position change region for the image pickup optical center of the distal end portion of the insertion section 11a.

As shown in FIGS. 12 and 13, the fixing implement F is attached to the access port AP provided in the casing C, and the insertion section 11a is passed through the insertion hole in the fixing implement F. The insertion section 11a is inserted toward an inner shroud SI by being passed through a hole H provided in an outer shroud SO in the stator S.

In the stator S, a plurality of stator vanes Sv are provided between the outer shroud SO and the inner shroud SI along the circumferential directions of the cylindrical outer and inner shrouds SO and SI. The insertion section 11a passed through the hole H is inserted between the two stator vanes Sv1 and Sv2.

The hole H in the form of a circular opening has such an inside diameter that when the insertion section 11a is passed through the hole H, a predetermined gap is formed between the periphery of the insertion section 11a and an inner edge portion of the hole H. Therefore, the user can move the distal end portion of the insertion section 11a in a predetermined region with the insertion section 11a as a pivot point Ph corresponding to a center of the insertion hole of the fixing implement F.

FIG. 14 shows a movable region MR for the insertion section 11a in the engine E. The user can move the insertion section 11a in the conical movable region MR indicated by broken lines in FIG. 14.

If the borescope 11B has the same insertion length L and attitude as those of the borescope 11A, the image pickup optical center Pc of the insertion section 11a is positioned on a circumference MRc of the bottom surface of the movable region MR. That is, the region in which the insertion section 11a of the borescope 11B can be moved so as to keep both the colors of the two match indicators 67 and 68 green after both the colors of the two match indicators 67 and 68 are changed from red to green as a result of steps S24 and S26 is limited to the circumference MRc of the bottom surface of the conical movable region MR.

In other words, the region in which the user can change the position of the image pickup optical center Pc of the insertion section 11a of the borescope 11B while maintaining the borescope 11B so that the insertion length and the attitude of the borescope 11B are not changed is limited to the circumference MRc of the bottom surface of the movable region MR.

Further, since the hole H in the outer shroud SO restricts the movement of the insertion section 11a, the region in which the image pickup optical center Pc of the insertion section 11a of the borescope 11B can be moved is only part of the circumference MRc of the bottom surface of the conical movable region MR. FIGS. 14 and 15 show that the region in which the user can move the image pickup optical center Pc of the insertion section 11a of the borescope 11B is limited to the part between points PL1 and PL2 on the circumference MRc.

Referring back to FIG. 10, while after S26 the user changes the position of the image pickup optical center Pc of the insertion section 11a of the borescope 11B while holding the borescope 11B so that the insertion length and the attitude of the borescope 11B are not changed, the CPU 51 executes in real time the determination as to whether there is a match between the two distance values d11 and d12 detected by the two distance sensors 31a and 31b and the two distance values d21 and d22 displayed in the distance information display portion 66B. That is, after S26, the CPU 51 determines whether there is a match between the two groups of distances (S27).

Note that in determination in S27 as to whether or not there is a match between the two groups of distances, it is determined that there is a match between the two groups of distances if the two distance values d11 and d12 detected by the two distance sensors 31a and 31b of the borescope 11B with which the current live image is being obtained fall within predetermined allowable ranges with respect to the distances d21 and d22 relating to the inspection image displayed in the image display portion 62B. For example, if the two distance values d11 and d12 are within a range from (d21−Δk3) to (d21+Δk3) and a range from (d22−Δk3) to (d22+Δk3), respectively, it is determined that there is a match between the two groups of distances.

If there is no match between the two groups of distances (S27: NO), the process returns to S22. If there is a match between the two groups of distances (S27: YES), the CPU 51 gives the match indicator 69 an indication in a predetermined color, green in the present embodiment (S28).

For example, referring to FIG. 15, when the image pickup optical center Pc of the insertion section 11a is located at a point Pp in a case where the image pickup optical center Pc is moved between the points PL1 and PL2 on the circumference MRc, a match may occur between the two distance values d11 and d12 detected by the two distance sensors 31a and 31b and the two distance values d21 and d22 displayed in the distance information display portion 66B. In such a case, at any one of points other than the point Pp, e.g., points Pp1 and Pp2, no match occurs between the two distance values d11 and d12 detected by the two distance sensors 31a and 31b and the two distance values d21 and d22 displayed in the distance information display portion 66B.

Figure 16:
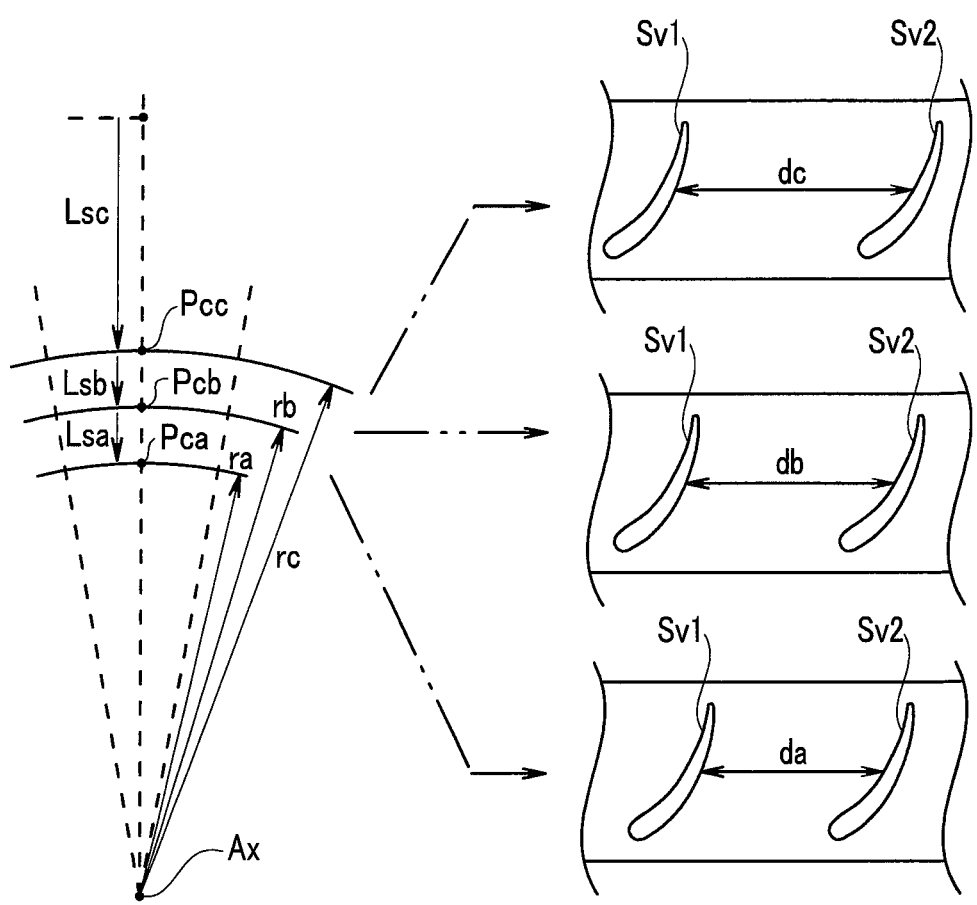
FIG. 16 is a diagram for explaining the relationship between the position of an image pickup optical center Pc of the insertion section 11a as seen in a direction along the axis of rotation Ax and two distance values d11 and d12 according to the first embodiment.

FIG. 16 is a diagram for explaining the relationship between the position of the image pickup optical center Pc of the insertion section 11a as seen in a direction along the axis of rotation Ax and the two distance values d11 and d12.

As shown in FIG. 16, the distance between two stator vanes Sv1 and Sv2 is changed between a state where the position of the image pickup optical center Pc is closer to the axis of rotation Ax and a state where the position of the image pickup optical center Pc is remoter from the axis of rotation Ax.

For example, in comparison between when the image pickup optical center Pc is positioned at an image pickup optical center Pca at a distance ra from the axis of rotation Ax and when the image pickup optical center Pc is positioned at an image pickup optical center Pcb at a distance rb remoter than the image pickup optical center Pca from the axis of rotation Ax, a distance da between central portions of the two stator vanes Sv1 and Sv2 at the image pickup optical center Pca is shorter than a distance db between central portions of the two stator vanes Sv1 and Sv2 at the image pickup optical center Pcb. This is because the stator vanes Sv1 and Sv2 respectively extend radially from the center of the axis of rotation Ax.

Similarly, in comparison between when the image pickup optical center Pc is positioned at the image pickup optical center Pcb at the distance rb from the axis of rotation Ax and when the image pickup optical center Pc is positioned at an image pickup optical center Pcc at a distance rc further remoter than the image pickup optical center Pcb from the axis of rotation Ax, the distance db between the central portions of the two stator vanes Sv1 and Sv2 at the image pickup optical center Pcb is shorter than a distance dc between central portions of the two stator vanes Sv1 and Sv2 at the image pickup optical center Pcc.

Conversely, if the insertion length L is increased, the distance between the two stator vanes Sv1 and Sv2 is reduced. As shown in FIG. 16, the distance db between the central portions of the stator vanes Sv1 and Sv2 when the insertion length L is an insertion length Lsb is longer than the distance da between the central portions of the stator vanes Sv1 and Sv2 when the insertion length L is an insertion length Lsa longer than the insertion length Lsb. Similarly, the distance dc between the central portions of the stator vanes Sv1 and Sv2 when the insertion length L is an insertion length Lsc is longer than the distance db between the central portions of the two stator vanes Sv1 and Sv2 when the insertion length L is an insertion length Lsb longer than the insertion length Lsc.

That is, if the insertion length L, the angle of elevation β and the angle of rotation γ are the same as the insertion length L, the angle of elevation β and the angle of rotation γ in the preceding inspection, a match occurs between the two distance values d21 and d22 detected by the two distance sensors 31a and 31b in the preceding inspection and the distance values d11 and d12 detected by the two distance sensors 31a and 31b of the borescope 11B only when the image pickup optical center Pc is located at the point Pp.

Thus, the viewing direction from the image pickup optical center Pcc is uniquely determined. In other words, the azimuth angle on the image pickup optical center Pcc is determined.

If a match occurs between two distance values da12 and da22 and the distance values d21 and d22 when the image pickup optical center Pc is located at the point Pp, as shown in FIG. 15, in a state where the borescope 11B is held so that the insertion length and the attitude of the borescope 11B are not changed, then no match occurs between two distance values da11 and da21 and the distance values d21 and d22, as shown in FIG. 15, when the image pickup optical center Pc is located at the point Pp1. Similarly, no match occurs between two distance values da13 and da23 and the distance values d21 and d22 when the image pickup optical center Pc is located at the point Pp2.

That is, the two distance values d11 and d12 detected by the two distance sensors 31a and 31b respectively match the two distance values d21 and d22 displayed in the distance information display portion 66B only when the image pickup optical center Pc is located at the point Pp.

If a match occurs between the two groups of distances (S27: YES), the CPU 51 gives the match indicator 69 an indication in a predetermined color, green in the present embodiment (S28). When the color of the match indicator 69 is green, the user can recognize the match between the two distance values d21 and d22 determined when the inspection image displayed in the image display portion 62B was obtained and the distance values d11 and d12 of the borescope 11B with which the current live image is being obtained.

Processing in S28 constitutes a match output section that, based on the result of comparison in S27, outputs match information indicating that there is a match between the two distance values d1 and d2 detected by the two distance sensors 31a and 31b of the borescope 11B and the two distance values d1 and d2 relating to the inspection image stored in the HDD 54 and displayed in the image display portion 62B. With the output of the predetermined match information as a result of processing in S28, the indication (color in the present embodiment) with the match indicator 69, which is a predetermined mark displayed on the LCD 55 provided as a display device, is changed.

In S24, S26, and S28 described above, the three match indicators 67, 68, and 69 indicate matches in insertion length, attitude and two distances d1 and d2, thereby enabling the user to observe an enlarged image of the blade B at the same position in the same viewing direction as at the time of obtaining the still image.

After processing in S28, the CPU 51 determines whether or not the image record button 70 has been selected or touched (S29). If the image record button 70 has not been selected (S29: NO), the process returns to S22.

If the image record button 70 has been selected (S29: YES), the CPU 51 produces a still image from the received live image and displays the still image in the image display portion 62A (S30).

The CPU 51 displays, in the insertion length information display portion 64A, the attitude information display portion 65A and the distance information display portion 66A, respectively, the insertion length, attitude information and position information determined when the still image displayed in the image display portion 62A was obtained (S31).

The CPU 51 determines whether or not the image record button 70 has been again selected or touched (S32). If the image record button 70 has not been selected (S32: NO), the CPU 51 determines whether or not the cancel button 73 has been selected (S33). If the cancel button 73 has been selected (S33: YES), the process returns to S22. If the cancel button 73 has not been selected, no processing is performed.

If the image record button 70 has been selected (S32: YES), the CPU 51 records, in the HDD 54 provided as a storage device, the still image displayed in the image display portion 62A, and the scope ID, the insertion length, the attitude information and the position information relating to the still image (S34).

As described above, the inspector can display on the LCD 55 a still image (enlarged still image) picked up at the same position and in the same direction as the position and direction of the image pickup optical center Pc set when the recorded inspection image was picked up, and can store the sill image in the HDD 54.

In the present embodiment, the scope ID, the insertion length, the attitude information and the position information relating to the still image are recorded as EXIF information of the image data in the HDD 54. However, the scope ID, the insertion length, the attitude information and the position information may alternatively be recorded in a file such as shown in FIG. 17, separately from the file for the still image.

FIG. 17 is a diagram showing the data structure of a photographing information recording file. As shown in FIG. 17, a photographing information recording file 81 has, as recording items, an image ID, a scope ID, an insertion length, an angle of elevation, an angle of rotation, a first distance and a second distance. The image ID is an image ID for image data on a still image, i.e., information for association with image data on a still image.

The scope ID, insertion length, angle of elevation, angle of rotation, first distance and second distance correspond to the above-described scope ID, insertion length L, angle of elevation $\beta$, angle of rotation $\gamma$, distance d21 and distance d22. In S8, S22, and S34 described above, these sorts of information including the scope ID are recorded in or read out from the photographing information recording file 81.

In the present embodiment, as described above, a blade inspection apparatus and method can be implemented that enable, in blade inspection, observation of a blade at the same position and in the same viewing direction as at the time of image pickup from the blade already performed to obtain an inspection image.

Second Embodiment

The blade inspection apparatus in the first embodiment is constructed so that a blade can be observed at the same position and in the same viewing direction as at the time of taking a still image to be recorded, based on the insertion length L, the angle of elevation $\beta$, the angle of rotation $\gamma$, and the two distances d1 and d2. A blade inspection apparatus in a second embodiment of the present invention is constructed so that a blade can be observed at the same position and in the same viewing direction as at the time of taking a still image to be recorded, based on the angle of elevation $\beta$, the angle of rotation $\gamma$, and the two distances d1 and d2 without using the insertion length L.

In the first embodiment, a possibility of the insertion section 11a supported by the fixing implement F being unable to be moved on only one fixed pivot point Ph because of the existence of a gap between the insertion hole of the fixing implement F and the insertion section 11a is considered and insertion assistance is performed based on the insertion length L, the angle of elevation $\beta$, the angle of rotation $\gamma$, and the two distances d1 and d2 next time the borescope is inserted. In the first embodiment, therefore, the insertion length L of the inserted borescope 11 is detected and a match between the detected insertion length L and the insertion length of the borescope 11 when a recorded still image was taken with the borescope 11 is determined before determination as to matches in the angle of elevation $\beta$, angle of rotation $\gamma$, and two distances d1 and d2.

However, if a fixing implement F that enables the insertion section 11a supported by the fixing implement F to move on one fixed pivot point Ph is used, the position of the distal end portion of the insertion section 11a from the access port AP can be determined only from the sum of the two distances d1 and d2 without detecting the insertion length L, since the distance between the two stator vanes changes so as to decrease gradually from the access port AP toward the axis of rotation, as described above with reference to FIG. 16.

Figure 18:
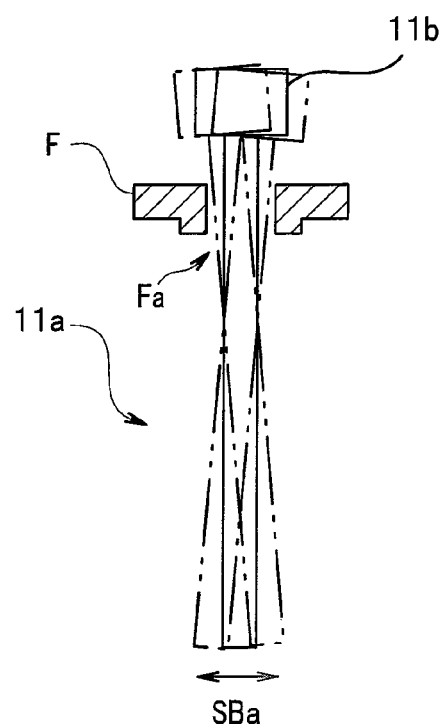
FIG. 18 is a diagram showing the state of deviation of the distal end portion of the insertion section 11a in a case where the opening diameter of an insertion hole Fa of a fixing implement F is large according to a second embodiment.
Figure 19:
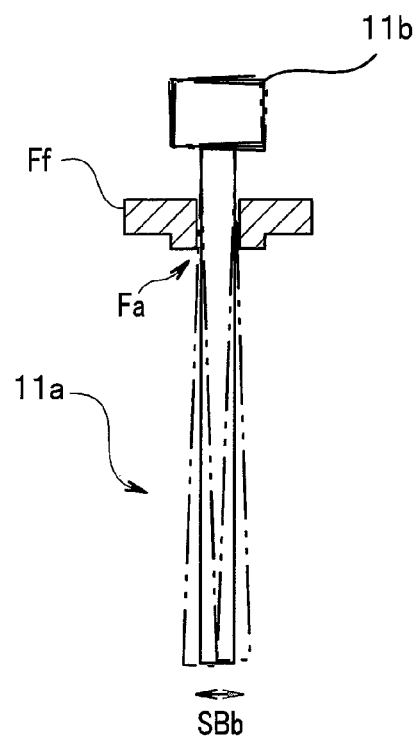
FIG. 19 is a diagram showing the state of deviation of the distal end portion of the insertion section 11a in a case where the opening diameter of an insertion hole Fa of a fixing implement Ff is small according to the second embodiment.

FIG. 18 is a diagram explaining the state of deviation of the distal end portion of the insertion section 11a in a case where the opening diameter of an insertion hole Fa of a fixing implement F is large. FIG. 19 is a diagram explaining the state of deviation of the distal end portion of the insertion section 11a in a case where the opening diameter of an insertion hole Fa of a fixing implement Ff is small.

The opening diameter of the insertion hole Fa of the fixing implement F shown in FIG. 18 is large, and the opening diameter of the insertion hole Fa of the fixing implement Ff shown in FIG. 19 is smaller than that of the insertion hole Fa of the fixing implement F. Therefore, the amount of deviation SBb of the distal end portion of the insertion section 11a in the case shown in FIG. 19 is smaller than the amount of deviation SBa of the distal end portion of the insertion section 11a in the case shown in FIG. 18.

If this amount of deviation SBb is sufficiently small, and if the position of the distal end portion of the insertion section 11a from the access port AP is uniquely determined only from the sum of the two distances d1 and d2, detection of the insertion length L is not required.

In the construction of the blade inspection system in the present embodiment is generally the same as the construction of the blade inspection system 1 shown in the first embodiment.

In the present embodiment, the distance sensor 32 used in the construction of the borescope 11 shown in FIGS. 2 and 3 according to the first embodiment is not required, while the acceleration sensor 27 and the two distance sensors 31a and 31b are required.

As a result, in the process shown in FIG. 8, information on the insertion length L not detected is neither displayed nor recorded.

In the GUI 61 shown in FIG. 9, the insertion length information display portions 64A and 64B and the match indicator 67 are not required, while the other components are required.

In the process shown in FIGS. 10 and 11, information on the insertion length L not detected is neither displayed nor recorded, and processing in step S23 and S24 is not required, while the other process steps are required. The unnecessary process steps are skipped and not executed.

Further, in the photographing information recording file, the insertion length item is unnecessary.

Thus, in the present embodiment, processing with the sensor for detecting the insertion length and processing relating to information on the insertion length are not performed since information on the insertion length is not used. However, determination is made as to a match between the two distances d1 and d2 detected by the two distance sensors 31a and 31b of the borescope 11B and the two distances d21 and d22 recorded in the HDD 54. Therefore, the user can insert the borescope 11B and determine the position and the viewing direction of the distal end portion of the insertion section 11a so that the position and the direction of the observation window are the same as at the time of finding a flaw or the like in the preceding inspection.

In the above-described two embodiments, as described above, a blade inspection apparatus and method can be implemented that enable, in blade inspection, observation of a blade at the same position and in the same viewing direction as at the time of image pickup from the blade already performed to obtain an inspection image.

The present invention is not limited to the above-described embodiments. Various changes and modifications can be made in the described embodiments without departing from the gist of the invention.

What is claimed is:

1. A blade inspection apparatus for inspecting a plurality of blades periodically disposed on a periphery of a rotating shaft of a rotor of an engine and rotated on the rotating shaft, the apparatus comprising:
    a first attitude detection section provided in a first endoscope having a first insertion section, the first attitude detection section detecting a first attitude of the first insertion section; and
    a first distance detection section provided in the first endoscope, the first distance detection section detecting two first distances from the first insertion section to two objects along two directions perpendicular to an axis of the first insertion section and opposite to each other.

2. The blade inspection apparatus according to claim 1, further comprising a first insertion length detection section that detects a first insertion length of the first insertion section of the first endoscope when the first insertion section is inserted through a hole provided in a casing in which the rotor is housed.

3. The blade inspection apparatus according to claim 2, further comprising:
    a storage section that, when a still image of the blades picked up by a second endoscope having a second insertion section, a second attitude detection section that detects a same attitude as the first attitude detected by the first attitude detection section, and a second distance detection section that detects same two distances as the first distances detected by the first distance detection section is obtained, stores a second attitude of the second insertion section detected by the second attitude detection section, and two second distances from the second insertion section detected by the second distance detection section;
    an attitude comparison section that makes a comparison between the first attitude detected by the first attitude detection section and the second attitude stored in the storage section;
    a distance comparison section that makes a comparison between the two first distances detected by the first distance detection section and the two second distances stored in the storage section;
    an insertion length comparison section that makes a comparison between the first insertion length detected by the first insertion length detection section and a second insertion length detected by a second insertion length detection section and stored in the storage section when the still image of the blade picked up by the second endoscope having the second insertion length detection section is obtained, the second insertion length detection section detecting a same insertion length as the insertion length detected by the first insertion length detection section;
    a first match output section that outputs match information indicating that there is a match between the first attitude and the second attitude based on a result of comparison made by the attitude comparison section;
    a second match output section that outputs match information indicating that there is a match between the two first distances and the two second distances based on a result of comparison made by the distance comparison section; and
    a third match output section that outputs match information indicating that there is a match between the first insertion length and the second insertion length based on a result of comparison made by the insertion length comparison section.

4. The blade inspection apparatus according to claim 3, wherein the first, second and third match output sections respectively output the first match information, the second match information and the third match information to change indications with predetermined first, second and third marks displayed on a display device.

5. The blade inspection apparatus according to claim 1, further comprising:
    a storage section that, when a still image of the blades picked up by a second endoscope having a second insertion section, a second attitude detection section that detects a same attitude as the first attitude detected by the first attitude detection section, and a second distance detection section that detects same two distances as the first distances detected by the first distance detection section is obtained, stores a second attitude of the second insertion section detected by the second attitude detection section, and two second distances from the second insertion section detected by the second distance detection section;

an attitude comparison section that makes a comparison between the first attitude detected by the first attitude detection section and the second attitude stored in the storage section;

a distance comparison section that makes a comparison between the two first distances detected by the first distance detection section and the two second distances stored in the storage section;

a first match output section that outputs match information indicating that there is a match between the first attitude and the second attitude based on a result of comparison made by the attitude comparison section; and a second match output section that outputs match information indicating that there is a match between the two first distances and the two second distances based on a result of comparison made by the distance comparison section.

6. The blade inspection apparatus according to claim 5, wherein the first and second match output sections respectively output the first match information and the second match information to change indications with predetermined first and second marks displayed on a display device.

7. The blade inspection apparatus according to claim 5, wherein the first and second attitudes are determined by inclinations of the first and second insertion sections from respective predetermined directions and by angles of rotation of the first and second insertion sections on the axis.

8. The blade inspection apparatus according to claim 1, wherein the two objects are stator vanes provided on a stator of the engine.

9. A blade inspection method of inspecting a plurality of blades periodically disposed on a periphery of a rotating shaft of a rotor of an engine and rotated on the rotating shaft, the method comprising:
detecting a first attitude of a first insertion section of a first endoscope with a first attitude detection section provided in the first endoscope; and
detecting two first distances from the first insertion section to two objects along two directions perpendicular to an axis of the first insertion section and opposite to each other with a first distance detection section provided in the first endoscope.

10. The blade inspection method according to claim 9, further comprising detecting a first insertion length of the first insertion section of the first endoscope when the first insertion section is inserted through a hole provided in a casing in which the rotor is housed.

11. The blade inspection method according to claim 10, further comprising:
making a comparison between a second attitude of a second insertion section of a second endoscope detected by a second attitude detection section when a still image of the blades picked up by the second endoscope is obtained and the first attitude detected by the first attitude detection section, the second attitude detection section being provided in the second endoscope, the second attitude detection section detecting a same attitude as the first attitude detected by the first attitude detection section;

making a comparison between two second distances from the second insertion section detected by a second distance detection section when the still image of the blade is obtained and the two first distances detected by the first distance detection section, the second distance detecting section being provided in the second endoscope, the second distance detection section detecting same two distances as the first distances detected by the first distance detection section;

making a comparison between a second insertion length of the second insertion section detected by a second insertion length detection section when the still image of the blade is obtained and the first insertion length detected by the first insertion length detection section, the second insertion length detection section being provided in the second endoscope, the second insertion length detection section detecting a same insertion length as the insertion length detected by the first insertion length detection section;

outputting first match information indicating that there is a match between the first attitude and the second attitude based on a result of comparison between the first attitude and the second attitude;

outputting second match information indicating that there is a match between the two first distances and the two second distances based on a result of comparison between the two first distances and the two second distances; and outputting third match information indicating that there is a match between the first insertion length and the second insertion length based on a result of comparison between the first insertion length and the second insertion length.

12. The blade inspection method according to claim 11, wherein the first match information, the second match information and the third match information are information items for changing indications with predetermined first, second and third marks displayed on a display device, respectively.

13. The blade inspection method according to claim 9, further comprising:
making a comparison between a second attitude of a second insertion section of a second endoscope detected by a second attitude detection section when a still image of the blades picked up by the second endoscope is obtained and the first attitude detected by the first attitude detection section, the second attitude detection section being provided in the second endoscope, the second attitude detection section detecting a same attitude as the first attitude detected by the first attitude detection section;

making a comparison between two second distances from the second insertion section detected by a second distance detection section when the still image of the blade is obtained and the two first distances detected by the first distance detection section, the second distance detecting section being provided in the second endoscope, the second distance detection section detecting same two distances as the first distances detected by the first distance detection section;

outputting first match information indicating that there is a match between the first attitude and the second attitude based on a result of comparison between the first attitude and the second attitude; and outputting second match information indicating that there is a match between the two first distances and the two second distances based on a result of comparison between the two first distances and the two second distances.

14. The blade inspection method according to claim 13, wherein the first match information and the second match information are information items for changing indications with predetermined first and second marks displayed on a display device, respectively.

15. The blade inspection method according to claim 9, wherein the first and second attitudes are determined by inclinations of the first and second insertion sections from respective predetermined directions and by angles of rotation of the first and second insertion sections on the axis.

16. The blade inspection method according to claim 9, wherein the two objects are stator vanes provided on a stator of the engine.

* * * * *